(12) United States Patent
Shiroff et al.

(10) Patent No.: US 9,999,763 B2
(45) Date of Patent: Jun. 19, 2018

(54) APPARATUS AND METHODS FOR ANCHORING ELECTRODE LEADS ADJACENT TO NERVOUS TISSUE

(71) Applicant: Mainstay Medical Limited, Swords, County Dublin OT (IE)

(72) Inventors: Jason Alan Shiroff, Edina, MN (US); Henry Thomas Demorett, Prior Lake, MN (US); Prashant Brijmohansingh Rawat, Blaine, MN (US); Johannes Petrus Heemels, Keerbergen (BE); Peter Andrew Crosby, Blaine, MN (US)

(73) Assignee: Mainstay Medical Limited, Swords, County Dublin (IE)

( * ) Notice: Subject to any disclaimer, the term of this patent is extended or adjusted under 35 U.S.C. 154(b) by 0 days. days.

(21) Appl. No.: 13/797,100

(22) Filed: Mar. 12, 2013

(65) Prior Publication Data

US 2013/0338730 A1 Dec. 19, 2013

Related U.S. Application Data

(60) Provisional application No. 61/659,334, filed on Jun. 13, 2012.

(51) Int. Cl.
*A61N 1/05* (2006.01)
*A61N 1/36* (2006.01)

(52) U.S. Cl.
CPC ........ *A61N 1/0558* (2013.01); *A61N 1/36057* (2013.01); *A61N 1/36071* (2013.01)

(58) Field of Classification Search
CPC ...... A61N 1/05; A61N 1/0551; A61N 1/0558; A61N 1/057
(Continued)

(56) References Cited

U.S. PATENT DOCUMENTS 3,077,884 A 2/1963 Bartow et al.
3,710,777 A 1/1973 Sparks
(Continued)

FOREIGN PATENT DOCUMENTS

CN 101678203 A 3/2010
EP 0 587 269 B1 12/1998
(Continued)

OTHER PUBLICATIONS

PCT International Search Report and Written Opinion dated Sep. 3, 2013 in related PCT Application No. PCT/US2013/045223.
(Continued)

*Primary Examiner* — Christopher A Flory
(74) *Attorney, Agent, or Firm* — Foley & Lardner LLP; Christopher C. Bolten; Nicola A. Pisano

(57) ABSTRACT

Apparatus for neuromuscular electrical stimulation and methods for anchoring the same are provided. The apparatus may include an elongated member having one or more electrodes disposed at the distal region of the elongated member and at least one fixation element disposed at the distal region of the elongated member. The fixation element may be shaped and sized to be deployed between tissue layers, such as muscle layers, without damaging the tissue layers so as to secure the one or more electrodes in or adjacent to a desired anatomical site within a patient. An additional fixation element may be disposed at the distal region of the elongated member so that tissue, such as a muscle, may be sandwiched between the fixation elements without damaging the tissue.

20 Claims, 19 Drawing Sheets

(58) Field of Classification Search
USPC .................................. 607/48, 116, 126, 149
See application file for complete search history.

(56) References Cited

U.S. PATENT DOCUMENTS

| | | | |
|---|---|---|---|
| 3,875,947 A | 4/1975 | Jula et al. |
| 3,893,463 A | 7/1975 | Williams |
| 3,999,551 A | 12/1976 | Spitz et al. |
| 4,010,757 A | 3/1977 | Jula et al. |
| 4,026,301 A | 5/1977 | Friedman et al. |
| 4,342,317 A | 8/1982 | Axelgaard |
| 4,408,609 A | 10/1983 | Axelgaard |
| 4,418,693 A | 12/1983 | Leveen et al. |
| 4,549,556 A | 10/1985 | Tarjan et al. |
| 4,574,806 A | 3/1986 | McCarthy |
| 4,658,835 A | 4/1987 | Pohndorf |
| 4,832,687 A | 5/1989 | Smith, III |
| 4,917,093 A | 4/1990 | Dufresne et al. |
| 5,069,680 A | 12/1991 | Grandjean |
| 5,199,430 A | 4/1993 | Fang et al. |
| 5,215,088 A | 6/1993 | Normann et al. |
| 5,273,053 A | 12/1993 | Pohndorf |
| 5,300,108 A | 4/1994 | Rebell et al. |
| 5,330,515 A | 7/1994 | Rutecki et al. |
| 5,496,345 A | 3/1996 | Kieturakis et al. |
| 5,501,452 A | 3/1996 | Halvorson |
| 5,507,788 A | 4/1996 | Lieber |
| 5,522,854 A | 6/1996 | Ideker et al. |
| 5,569,183 A | 10/1996 | Kieturakis |
| 5,638,825 A | 6/1997 | Yamazaki et al. |
| 5,733,307 A | 3/1998 | Dinsdale |
| 5,741,321 A * | 4/1998 | Brennen ....................... 607/127 |
| 5,782,841 A | 7/1998 | Ritz et al. |
| 5,807,234 A | 9/1998 | Bui et al. |
| 5,873,900 A | 2/1999 | Maurer et al. |
| 5,916,172 A | 6/1999 | Hodges et al. |
| 5,957,968 A * | 9/1999 | Belden .................. A61N 1/057 |
| | | | 604/175 |
| 6,104,957 A | 8/2000 | Alo et al. |
| 6,119,516 A | 9/2000 | Hock |
| 6,314,325 B1 | 11/2001 | Fitz |
| 6,319,241 B1 | 11/2001 | King et al. |
| 6,324,414 B1 | 11/2001 | Gibbons et al. |
| 6,366,819 B1 | 4/2002 | Stokes |
| 6,406,421 B1 | 6/2002 | Grandjean et al. |
| 6,473,654 B1 | 10/2002 | Chinn |
| 6,516,227 B1 | 2/2003 | Meadows et al. |
| 6,527,787 B1 | 3/2003 | Fogarty et al. |
| 6,565,594 B1 | 5/2003 | Herweck et al. |
| 6,600,954 B2 | 7/2003 | Cohen et al. |
| 6,600,956 B2 | 7/2003 | Maschino et al. |
| 6,605,094 B1 | 8/2003 | Mann et al. |
| 6,671,557 B1 | 12/2003 | Gliner |
| 6,735,474 B1 * | 5/2004 | Loeb ................. A61N 1/36007 |
| | | | 607/41 |
| 6,839,594 B2 | 1/2005 | Cohen et al. |
| 6,845,271 B2 | 1/2005 | Fang et al. |
| 7,018,384 B2 | 3/2006 | Skakoon |
| 7,096,070 B1 | 8/2006 | Jenkins et al. |
| 7,206,641 B2 | 4/2007 | Ignagni et al. |
| 7,218,970 B2 | 5/2007 | Ley et al. |
| 7,239,918 B2 | 7/2007 | Strother et al. |
| 7,286,879 B2 | 10/2007 | Wallace |
| 7,317,948 B1 | 1/2008 | King et al. |
| 7,324,852 B2 | 1/2008 | Barolat et al. |
| 7,324,853 B2 | 1/2008 | Ayal et al. |
| 7,337,005 B2 | 2/2008 | Kim et al. |
| 7,337,006 B2 | 2/2008 | Kim et al. |
| 7,369,894 B2 | 5/2008 | Gerber |
| 7,389,149 B2 | 6/2008 | Rossing et al. |
| 7,444,181 B2 | 10/2008 | Shi et al. |
| 7,447,546 B2 | 11/2008 | Kim et al. |
| 7,450,993 B2 | 11/2008 | Kim et al. |
| 7,489,561 B2 | 2/2009 | Armstrong et al. |
| 7,493,175 B2 | 2/2009 | Cates et al. |
| 7,499,746 B2 | 3/2009 | Buhlmann et al. |
| 7,502,651 B2 | 3/2009 | Kim et al. |
| 7,580,753 B2 * | 8/2009 | Kim ..................... A61N 1/0558 |
| | | | 607/46 |
| 7,668,598 B2 | 2/2010 | Herregraven et al. |
| 7,684,866 B2 | 3/2010 | Fowler et al. |
| 7,708,763 B2 | 5/2010 | Selovar et al. |
| 7,761,166 B2 | 7/2010 | Giftakis et al. |
| 7,792,591 B2 | 9/2010 | Rooney et al. |
| 7,797,053 B2 * | 9/2010 | Atkinson .................. A61F 2/86 |
| | | | 607/115 |
| 7,813,803 B2 | 10/2010 | Heruth et al. |
| 7,908,015 B2 * | 3/2011 | Lazeroms ............ A61N 1/0504 |
| | | | 607/116 |
| 7,917,230 B2 | 3/2011 | Bly |
| 7,930,039 B2 | 4/2011 | Olson |
| 7,981,144 B2 | 7/2011 | Geist et al. |
| 8,016,846 B2 | 9/2011 | McFarlin et al. |
| 8,065,020 B2 | 11/2011 | Ley et al. |
| 8,082,039 B2 | 12/2011 | Kim et al. |
| 8,170,690 B2 * | 5/2012 | Morgan ............... A61N 1/0573 |
| | | | 607/116 |
| 8,229,565 B2 | 7/2012 | Kim et al. |
| 8,229,656 B2 | 7/2012 | Ikushima et al. |
| 8,249,701 B2 | 8/2012 | Imran et al. |
| 8,249,713 B2 | 8/2012 | Fang et al. |
| 8,380,318 B2 | 2/2013 | Kishawi et al. |
| 8,391,966 B2 | 3/2013 | Luo et al. |
| 8,409,233 B1 | 4/2013 | Chinn et al. |
| 8,428,728 B2 | 4/2013 | Sachs |
| 8,463,383 B2 | 6/2013 | Sakai et al. |
| 8,498,697 B2 | 7/2013 | Yong et al. |
| 8,606,358 B2 | 12/2013 | Sachs |
| 8,798,005 B1 | 8/2014 | Vargantwar et al. |
| 8,886,337 B2 | 11/2014 | Bennett et al. |
| 8,965,516 B2 | 2/2015 | Bennett et al. |
| 9,072,897 B2 | 7/2015 | Sachs et al. |
| 9,079,019 B2 | 7/2015 | Crosby et al. |
| 9,108,053 B2 | 8/2015 | Crosby et al. |
| 9,561,364 B2 | 2/2017 | Bondhus |
| 2001/0053885 A1 | 12/2001 | Gielen et al. |
| 2002/0065543 A1 | 5/2002 | Gomperz et al. |
| 2002/0099419 A1 | 7/2002 | Cohen et al. |
| 2002/0115945 A1 | 8/2002 | Herman et al. |
| 2002/0156513 A1 | 10/2002 | Borkan |
| 2002/0161415 A1 | 10/2002 | Cohen et al. |
| 2002/0183765 A1 * | 12/2002 | Adams ........................ 606/139 |
| 2003/0100933 A1 | 5/2003 | Ayal et al. |
| 2003/0120328 A1 | 6/2003 | Jenkins et al. |
| 2003/0199938 A1 | 10/2003 | Smits et al. |
| 2004/0030360 A1 | 2/2004 | Eini et al. |
| 2004/0097986 A1 * | 5/2004 | Adams ........................ 606/151 |
| 2004/0111118 A1 | 6/2004 | Hill et al. |
| 2004/0122482 A1 | 6/2004 | Tung et al. |
| 2004/0147969 A1 * | 7/2004 | Mann et al. .................... 607/17 |
| 2004/0167580 A1 * | 8/2004 | Mann et al. .................... 607/17 |
| 2004/0214790 A1 | 10/2004 | Borgens |
| 2004/0230281 A1 | 11/2004 | Heil et al. |
| 2004/0236383 A1 | 11/2004 | Yelizarov |
| 2005/0075701 A1 | 4/2005 | Shafer |
| 2005/0080472 A1 | 4/2005 | Atkinson et al. |
| 2005/0107861 A1 | 5/2005 | Harris et al. |
| 2005/0119713 A1 | 6/2005 | Whitehurst et al. |
| 2005/0149154 A1 | 7/2005 | Cohen et al. |
| 2005/0154389 A1 | 7/2005 | Selover et al. |
| 2005/0165456 A1 * | 7/2005 | Mann et al. .................... 607/30 |
| 2005/0177211 A1 | 8/2005 | Leung et al. |
| 2005/0240243 A1 | 10/2005 | Barolat et al. |
| 2005/0246006 A1 | 11/2005 | Daniels |
| 2005/0283204 A1 | 12/2005 | Buhlmann et al. |
| 2006/0009810 A1 * | 1/2006 | Mann et al. .................... 607/17 |
| 2006/0009827 A1 | 1/2006 | Kurth et al. |
| 2006/0032657 A1 | 2/2006 | Zarembo |
| 2006/0052856 A1 | 3/2006 | Kim et al. |
| 2006/0106416 A1 | 5/2006 | Raymond et al. |
| 2006/0111746 A1 | 5/2006 | Foreman et al. |
| 2006/0111754 A1 | 5/2006 | Rezai et al. |
| 2006/0184222 A1 | 8/2006 | Camps et al. |
| 2006/0206166 A1 | 9/2006 | Weiner |

(56) References Cited

U.S. PATENT DOCUMENTS

| | | |
|---|---|---|
| 2006/0235484 A1 | 10/2006 | Jaax et al. |
| 2006/0241716 A1 | 10/2006 | Finch et al. |
| 2006/0259074 A1* | 11/2006 | Kelleher et al. ............ 606/213 |
| 2007/0027501 A1 | 2/2007 | Jensen et al. |
| 2007/0049980 A1 | 3/2007 | Zielinski et al. |
| 2007/0060967 A1 | 3/2007 | Strother et al. |
| 2007/0073357 A1* | 3/2007 | Rooney et al. ................ 607/46 |
| 2007/0100377 A1 | 5/2007 | Armstrong et al. |
| 2007/0100391 A1 | 5/2007 | Armstrong |
| 2007/0100408 A1 | 5/2007 | Gerber |
| 2007/0100411 A1* | 5/2007 | Bonde ........................ 607/126 |
| 2007/0123954 A1 | 5/2007 | Gielen et al. |
| 2007/0129780 A1 | 6/2007 | Whitehurst et al. |
| 2007/0135768 A1 | 6/2007 | Carlsen |
| 2007/0179557 A1 | 8/2007 | Maschino et al. |
| 2007/0208392 A1 | 9/2007 | Kuschner et al. |
| 2007/0232936 A1* | 10/2007 | Mann et al. ................. 600/486 |
| 2007/0239224 A1 | 10/2007 | Bennett et al. |
| 2008/0026981 A1 | 1/2008 | Muhrer et al. |
| 2008/0103573 A1 | 5/2008 | Gerber |
| 2008/0103579 A1 | 5/2008 | Gerber |
| 2008/0132961 A1 | 6/2008 | Jaax et al. |
| 2008/0132969 A1 | 6/2008 | Bennett et al. |
| 2008/0167698 A1 | 7/2008 | Kim et al. |
| 2008/0177351 A1 | 7/2008 | Fang et al. |
| 2008/0183221 A1 | 7/2008 | Burdulis |
| 2008/0183257 A1 | 7/2008 | Imran et al. |
| 2008/0200972 A1 | 8/2008 | Rittman et al. |
| 2008/0228241 A1* | 9/2008 | Sachs ............................ 607/48 |
| 2008/0234791 A1 | 9/2008 | Arle et al. |
| 2008/0269716 A1 | 10/2008 | Bonde et al. |
| 2008/0269812 A1 | 10/2008 | Gerber et al. |
| 2009/0005833 A1 | 1/2009 | Cameron et al. |
| 2009/0018576 A1* | 1/2009 | Binmoeller ................. 606/215 |
| 2009/0112263 A1 | 4/2009 | Pool et al. |
| 2009/0192567 A1 | 7/2009 | Armstrong et al. |
| 2009/0210041 A1 | 8/2009 | Kim et al. |
| 2009/0248095 A1 | 10/2009 | Schleicher et al. |
| 2009/0254095 A1 | 10/2009 | Levine et al. |
| 2009/0259280 A1 | 10/2009 | Wilkin et al. |
| 2009/0299201 A1 | 12/2009 | Gunderson |
| 2009/0326613 A1 | 12/2009 | Knoblich |
| 2010/0030227 A1 | 2/2010 | Kast et al. |
| 2010/0036280 A1 | 2/2010 | Ballegaard et al. |
| 2010/0036454 A1 | 2/2010 | Bennett et al. |
| 2010/0082086 A1 | 4/2010 | Zhu |
| 2010/0114206 A1 | 5/2010 | Kaemmerer et al. |
| 2010/0137938 A1 | 6/2010 | Kishawi et al. |
| 2010/0152808 A1 | 6/2010 | Boggs, II |
| 2010/0152809 A1 | 6/2010 | Boggs, II |
| 2010/0174240 A1 | 7/2010 | Wells et al. |
| 2010/0174326 A1 | 7/2010 | Selover et al. |
| 2010/0179562 A1 | 7/2010 | Linker et al. |
| 2010/0185161 A1 | 7/2010 | Pellegrino et al. |
| 2010/0211149 A1 | 8/2010 | Morgan et al. |
| 2010/0249875 A1 | 9/2010 | Kishawi et al. |
| 2010/0280576 A1 | 11/2010 | Gerber et al. |
| 2010/0292769 A1 | 11/2010 | Brounstein et al. |
| 2011/0004269 A1 | 1/2011 | Strother et al. |
| 2011/0021943 A1 | 1/2011 | Lacour et al. |
| 2011/0022114 A1 | 1/2011 | Navarro |
| 2011/0022123 A1 | 1/2011 | Stancer et al. |
| 2011/0054565 A1 | 3/2011 | Wacnik et al. |
| 2011/0106207 A1 | 5/2011 | Cauller et al. |
| 2011/0160538 A1* | 6/2011 | Ravikumar et al. .......... 600/204 |
| 2011/0224665 A1 | 9/2011 | Crosby et al. |
| 2011/0224682 A1 | 9/2011 | Westlund et al. |
| 2011/0251662 A1 | 10/2011 | Griswold et al. |
| 2011/0270340 A1 | 11/2011 | Pellegrini et al. |
| 2012/0035953 A1 | 2/2012 | Armstrong |
| 2012/0089153 A1 | 4/2012 | Christopherson et al. |
| 2012/0116477 A1 | 5/2012 | Crowe et al. |
| 2012/0192874 A1 | 8/2012 | Bolea et al. |
| 2012/0215218 A1 | 8/2012 | Lipani |
| 2012/0283800 A1 | 11/2012 | Perryman et al. |
| 2012/0290055 A1 | 11/2012 | Boggs, II |
| 2012/0310140 A1 | 12/2012 | Kramer et al. |
| 2012/0310301 A1 | 12/2012 | Bennett et al. |
| 2012/0310302 A1 | 12/2012 | Bennett et al. |
| 2012/0310314 A1 | 12/2012 | Bennett et al. |
| 2012/0323253 A1 | 12/2012 | Garai et al. |
| 2013/0023974 A1 | 1/2013 | Amrani |
| 2013/0096641 A1 | 4/2013 | Strother et al. |
| 2013/0131766 A1 | 5/2013 | Crosby et al. |
| 2013/0155117 A1 | 6/2013 | Bang |
| 2013/0197607 A1 | 8/2013 | Wilder et al. |
| 2013/0197615 A1 | 8/2013 | Rundle et al. |
| 2013/0211487 A1 | 8/2013 | Fang et al. |
| 2013/0238066 A1 | 9/2013 | Boggs et al. |
| 2013/0245715 A1 | 9/2013 | Sharek-Evans et al. |
| 2013/0261696 A1 | 10/2013 | Thacker et al. |
| 2013/0296966 A1 | 11/2013 | Wongsarnpigoon et al. |
| 2013/0310901 A1 | 11/2013 | Perryman et al. |
| 2014/0039574 A1 | 2/2014 | Bradley |
| 2014/0046398 A1 | 2/2014 | Sachs et al. |
| 2014/0058476 A1 | 2/2014 | Crosby et al. |
| 2014/0114385 A1 | 4/2014 | Nijhuis et al. |
| 2014/0288616 A1 | 9/2014 | Rawat et al. |
| 2014/0350653 A1 | 11/2014 | Shiroff et al. |
| 2015/0105840 A1 | 4/2015 | Boggs, II |
| 2015/0306405 A1 | 10/2015 | Sachs et al. |
| 2015/0374992 A1 | 12/2015 | Crosby et al. |
| 2016/0045746 A1 | 2/2016 | Jiang et al. |
| 2016/0045747 A1 | 2/2016 | Jiang et al. |
| 2016/0067476 A1 | 3/2016 | Rawat et al. |
| 2016/0106994 A1 | 4/2016 | Crosby et al. |
| 2016/0213927 A1 | 7/2016 | McGee et al. |

FOREIGN PATENT DOCUMENTS

| | | |
|---|---|---|
| EP | 1 053 762 B1 | 11/2000 |
| EP | 1 255 583 A1 | 11/2002 |
| EP | 2 273 931 A1 | 1/2011 |
| WO | WO-01/58520 A1 | 8/2001 |
| WO | WO-2004/066820 A2 | 8/2004 |
| WO | WO-2006/091611 A1 | 8/2006 |
| WO | WO-2006/133445 A2 | 12/2006 |
| WO | WO 2006/135791 A2 | 12/2006 |
| WO | WO 2007/051146 A1 | 5/2007 |
| WO | WO-2007/138598 A2 | 12/2007 |
| WO | WO 2008/048471 A2 | 4/2008 |
| WO | WO-2008/070807 A2 | 6/2008 |
| WO | WO-2008/094952 A2 | 8/2008 |
| WO | WO-2008/112178 A1 | 9/2008 |
| WO | WO-2009/020764 A1 | 2/2009 |
| WO | WO-2009/134475 A1 | 11/2009 |
| WO | WO-2010/062600 A2 | 6/2010 |
| WO | WO-2010/062622 A2 | 6/2010 |
| WO | WO-2011/079866 A1 | 7/2011 |
| WO | WO-2011/112773 A2 | 9/2011 |
| WO | WO-2012/057916 A1 | 5/2012 |
| WO | WO-2012/091747 A1 | 7/2012 |
| WO | WO-2013/016268 A1 | 1/2013 |
| WO | WO-2013/019853 A1 | 2/2013 |
| WO | WO-2013/036630 A1 | 3/2013 |
| WO | WO-2013/096260 A1 | 6/2013 |
| WO | WO-2013/155117 A1 | 10/2013 |
| WO | WO-2014/099423 A1 | 6/2014 |
| WO | WO-2015/059570 A1 | 4/2015 |
| WO | WO-2015/187426 A1 | 12/2015 |

OTHER PUBLICATIONS

Garmirian, et al., "Discriminating Neurogenic from Myopathic Disease via Measurement of Muscle Anisotrophy," Muscle Nerve, 39(1):16-24 (2009) (Abstract only).

Hodges, et al., "Intervertebral Stiffness of the Spine is Increased by Evoked Contraction of Transversus Abdominis and the Diaphragm: In Vivo Porcine Studies," Spine 28(23):2594-2601 (2003) (Abstract only).

Hodges, "Is There a Role for Transversus Abdominis in Lumbo-Pelvis Stability?" Manual Therapy, 4(2):74-86 (1999).

(56) References Cited

OTHER PUBLICATIONS

Holm, et al., "Sensorimotor Control of the Spine," J. Electromyogr. Kinesiol. 12(3):219-34 (2002) (Abstract only).
Keller, et al., "Muscular Contributions to Dynamic Dorsoventral Lumber Spine Stiffness," Eur. Spine J., 16(2):245-54 (2007).
Miyatani, et al., "Validity of Estimating Limb Muscle Volume by Bioelectrical Impedance," J. Appl. Physiol., 91:386-394 (2001).
Rutkove, "Electrical Impedance Myography: Background, Current State, and Future Directions," Muscle Nerve, 40(6):936-946 (2009).
Solomonow et al., "The Ligamento-Muscular Stabilizing System of the Spine," Spine, (1998), 23(23):2552-2562.
Stokes, et al., "Surface EMG Electrodes Do Not Accurately Record from Lumbar Multifidus Muscles," Clin. Biomech, (2003), 18(1):9-13 (Abstract Only).
Van Dieen, et al., "Trunk Muscle Recruitment Patterns in Patients With Low Back Pain Enhance the Stability of the Lumbar Spine," Spine, (2003), 28(8):834-841 (Abstract Only).
Verrills et al., "Peripheral Nerve Stimulation: A Treatment for Chronic Low Back Pain and Failed Back Surgery Syndrome?," Neuromodulation: Technology at the Neural Interface, (2009), 12(1):68-75.
Airaksinen et al., "Chapter 4. European guidelines for the management of chronic nonspecific low back pain," European spine journal [I: official publication of the European Spine Society, the European Spinal Deformity Society, and the European Section of the Cervical Spine Research Society 15 Suppl 2 (2006):S192-300. http://www.ncbi.nlm.nih.gov/pubmed/16550448.
Baker et al., "Clinical Uses of Neuromuscular Electrical Stimulation," NeuroMuscular Electrical Stimulation—A Practical Guide, 4th ed. Rancho Los Amigos Research and Education Institute Inc., pp. 47-66 (2000).
Bhadra et al., "Peripheral nerve stimulation for restoration of motor function," Journal of Clinical Neurophysiology: Official Publication of the American Electroencephalographic Society, 14(5):378-33 (Sep. 1997).
Bogie et al., "Effects of regular use of neuromuscular electrical stimulation on tissue health," Journal of Rehabilitation Research and Development, 40(6):469-475 (2003) available at: http://www.ncbi.nlm.nih.gov/pubmed/15077659 (Accessed Jan. 18, 2011).
Bowman et al., "Effects of Waveform Parameters on Comfort during Transcutaneous Neuromuscular Electrical Stimulation," Annals of Biomedical Engineering, 13:59-74 (1985).
Bradford et al., "Surface Electrical Stimulation in the Treatment of Idiopathic Scoliosis: Preliminary Results in 30 Patients," Spine, 8(7):757-764 (1983).
Brazier et al., "A Comparison of the EQ-5D and SF-6D Across Seven Patient Groups," Health Economics, 13:873-884 (2004).
Coghlan et al., "Electrical muscle stimulation for deep stabilizing muscles in abdominal wall," Conference proceedings: . . . Annual International Conference of the IEEE Engineering in Medicine and Biology Society. IEEE Engineering in Medicine and Biology Society. Conference, pp. 2756-2759 (2008) available at: http://www.ncbi.nlm.nih.gov/pubmed/19163276.
Coghlan et al., "Neuromuscular electrical stimulation training results in enhanced activation of spinal stabilizing muscles during spinal loading and improvements in pain ratings," Conference proceedings: . . . Annual International Conference of the IEEE Engineering in Medicine and Biology Society. IEEE Engineering in Medicine and Biology Society. Conference, pp. 7622-7625 (2011) available at: http://www.ncbi.nlm.nih.gov/pubmed/22256103.
Crago et al., "The choice of pulse duration for chronic electrical stimulation via surface, nerve, and intramuscular electrodes," Annals of Biomedical Engineering, 2(3):252-264 (1974).
Criterion Inc., "NMES Treatment Protocols," 3 pages (accessed Jun. 7, 2012) available at http://www.criterionmed.com/PDF/NMES%20Treatment%20Protocols.pdf.
Durham et al., "Surface Electrical Stimulation Versus Brace in Treatment of Idiopathic Scoliosis," Spine, 15(9):888-891 (1990).
Empi, "Low Back Syndrome/Chronic Low Back Pain," NMES Guidelines for Treatment, 2 pages (2003).

Ferreira et al., "Comparison of general exercise, motor control exercise and spinal manipulative therapy for chronic low back pain: A randomized trial," Pain, 131(1-2):31-37 (2007) available at: http://www.ncbi.nlm.nih.gov/pubmed/17250965.
Friedman et al., "Electrical stimulation for scoliosis," American Family Physician, 25(4):155-160 (1982) available at: http://www.ncbi.nlm.nih.gov/pubmed/6978055 (Accessed Oct. 19, 2011).
Gazelle et al., "Tumor Ablation with radio-frequency Energy," Radiology, (2000), 217(3):633-646.
Glaser et al., "Electrical Muscle Stimulation as an Adjunct to Exercise Therapy in the Treatment of Nonacute Low Back Pain: A Randomized Trial," The Journal of Pain, 2(5):295-300 (2001).
Gondin, et al., Electromyostimulation training effects on neural drive and muscle architecture, Med. Sci. Sports. Exerc., 37(8):1291-9 (2005).
Gorman et al., "The effect of stimulus parameters on the recruitment characteristics of direct nerve stimulation," IEEE Transactions on Bio-medical Engineering, 30(7):407-414 (1983).
Haemmerich et al., "Thermal Tumor Ablation: Devices, Clinical Applications and Future Directions," Int. J. Hyperthermia, (2005) 21(8):775-760 (Abstract).
Hagg et al., "The Clinical Importance of Changes in Outcome Scores After Treatment for Chronic Low Back Pain," Eur. Spine. J., 12:12-20 (2003).
Herbert et al., "Scoliosis Treatment in Children Using a Programmable, Totally Implantable Muscle Stimulator (ESI)," IEEE Transactions on Biomedical Engineering, 36(7):801 (Jul. 1989).
Hodges et al., "Response of the deep paraspinal muscles to cortical but not transmastoid stimulation is increased at a single lumbar level following intervertebral disc lesion," Progress in Motor Control Vi—Brazil. 36:2-3 (2007).
Hortobagyi et al., "Neural adaptations to electrical stimulation strength training," European Journal of Applied Physiology, 2439-2449 (2011) available at: http://www.ncbi.nlm.nih.gov/pubmed/21643920 (Accessed Jul. 19, 2011).
Informal Response to Written Opinion dated Jan. 17, 2012 in Int'l PCT Patent Appl. Serial No. PCT/US2011/027834.
International Search Report & Written Opinion dated Jan. 19, 2016 in Int'l PCT Patent Appl. Serial No. PCT/IB2015/055926.
International Search Report & Written Opinion dated Apr. 5, 2013 in Int'l PCT Patent Application Serial No. PCT/US2012/070259.
International Search Report & Written Opinion dated Jun. 25, 2008 in Int'l PCT Patent Appl No. PCT/US08/03126.
International Search Report and Written Opinion dated Jan. 26, 2016 in Int'l PCT Patent Appl. Serial No. PCT/IB2015/057838.
International Search Report and Written Opinion dated Oct. 16, 2015 in Int'l PCT Patent Appl Serial No. PCT/US2015/032732.
International Search Report dated Oct. 19, 2011 in Int'l PCT Patent Appl. Serial No. PCT/US2011/027934.
Kiesel et al., "Measurement of lumbar multifidus muscle contraction with rehabilitative ultrasound imaging," Manual Therapy, 12(2):161-166 (2007) available at: http://www.ncbi.nlm.nih.gov/pubmed/16973400.
Lauridsen et al., "Responsiveness and Minimal Clinically Important Difference for Pain and Disability Instruments in Low Back Pain Patients," BMC Musculoskeletal Disorders, 7(82):16 pages (2006).
Lieber, Richard, Comparison between animal and human studies of skeletal muscle adaptation to chronic stimulation, Clinical Orthopaedics and related research, No. 233, pp. 19-24 (1988).
Lieber, Richard, Skeletal muscle adaptability. II: Muscle properties following spinal-cord injury, Developmental medicine and Child Neurology 28(4):533-42 (1986).
Lieber, Richard, Skeletal muscle adaptability. III: Muscle properties following chronic electrical stimulation, Developmental medicine and Child Neurology 28(5):662-70 (1986).
Mortimer et al., "Intramuscular electrical stimulation: tissue damage," Annals of Biomedical Engineering, 8(3):235-244 (1980).
Mortimer et al., "Peripheral Nerve and Muscle Stimulation. In: Horch KW, Dhillon G, eds," Neuroprosthetics: Theory and Practice (Series on Bioengineering & Biomedical Engineering—vol. (2), World Scientific Publishing Company, pp. 1-48 (2005).

(56) References Cited

OTHER PUBLICATIONS

Nachemson et al., "Effectiveness of Treatment with a Brace in Girls Who Have Adolescent Idiopathic Scoliosis," The Journal of Bone and Joint Surgery, 77-A(6):815-819 (Jun. 1995).
Oaao Bock, "ActiGait Implantable Drop Foot Stimulator," Surgeon Manual, 28 pages (2006).
O'Donnell et al., "Electrical Stimulation in the Treatment of Idiopathic Scoliosis," Clinical Orthopaedics and Related Research, No. 229:107-112 (Apr. 1988).
Paicius et al., "Peripheral Nerve Field Stimulation for the Treatment of Chronic Low Back Pain: Preliminary Results of Long-Term Follow-up: A Case Series," Neuromodulation, 10(3):279-290 (2007) available at: http://www.blackwell-synergy.com/doi/abs/I0.IIII/j.1525-1403.2007.00116.x.
Panjabi, Manohar, "A hypothesis of chronic back pain: ligament subfailure injuries lead to muscle control dysfunction," European spine journal: official publication of the European Spine Society, the European Spinal Deformity Society, and the European Section of the Cervical Spine Research Society 15, No. 5 (May 2006): 668-676. http://www.ncbi.nlm.nih.gov/pubmed/16047209.
Panjabi, Manohar, "The stabilizing system of the spine. Part 1. Function, dysfunction, adaptation, and enhancement," Journal of Spinal Disorders, 5(4)383-389 (Dec. 1992), Discussion 397. http://www.ncbi.nlm.nih.gov/pubmed/1490034.
Panjabi, Manohar, "The stabilizing system of the spine. Part II. Neutral zone and instability hypothesis," Journal of Spinal Disorders, 5(4):390-396 (Dec. 1992), Discussion 397. http://www.ncbi.nlm.nih.gov/pubmed/1490035.
Peckham et al., "Functional electrical stimulation for neuromuscular applications," Annual review of Biomedical Engineering, 7:327-360 (2005) available at: http://www.ncbi.nlm.nih.gov/pubmed/16004574.
Peterson et al., "Long-term intramuscular electrical activation of the phrenic nerve: safety and reliability," IEEE Transactions on Biomedical Engineering, 41(12):1115-1126 (1994).
Poitras et al., "Evidence-informed management of chronic low back pain with transcutaneous electrical nerve stimulation, interferential current, electrical muscle stimulation, ultrasound, and thermotherapy," The Spine Journal 8:226-233 (2008).
Reed B., :The Physiology of Neuromuscular Electrical Stimulation, Pediatric Physical Therapy, 9(3):96-102 (1997) available at: http://journals.lww.com/pedpt/pages/artic1eviewer.aspx?year=1997&issue=00930&article=00002&type=abstract.
Rosatelli, et al., Three-dimensional study of the musculotendinous architecture of lumbar multifidus and its functional implications, Clinical Anatomy 21(6):539-44 (2008).
RS Medical, "RS-4M Muscle Stimulator," available at http://www.rsmedical.com/documents/fact_sheet_RS4m.pdf (last visited Jul. 19, 2012).
Schwartz et al., "Therapeutic Electrical Stimulation of the Hypoglossal Nerve in Obstructive Sleep Apnea," Arch Otolaryngal Head Neck Surg., 127:1216-1223 (2001).
Sheffler et al., "Neuromuscular Electrical Stimulation in Neurorehabilitation," Muscle Nerve, 35:562-590 (2007).
Sippl, Charles J., "Computer Dictionary: Third Edition," pp. 2257 and 340.
Sluijter, "Radiofrequency Ablation in the Management of Spinal Pain," C212, (2006), IV(1):10-15.
Spinal Fusion Guidelines, MD Guidelines, 2009. www.mdguidelines.com/spinal-fusion.
Van et al., "The use of real-time ultrasound imaging for biofeedback of lumbar multifidus muscle contraction in healthy subjects," The Journal of Orthopaedic and Sports Physical Therapy, 36(12):920-925 (2006) available at: http://www.ncbi.nlm.nih.gov/pubmed/17193869.
Van Zundert et al., "Radiofrequency treatment for chronic pain syndromes," CPD Anaesthesis, 6(1):13-17 (2004).
Vrbova et al., Application of Muscle/Nerve Stimulation in Health and Disease, Springer Verlag (2008) available at: http://books.google.com/books?hl=en&lr=&id=jb8fDGxkbqEC&oi=fnd&pg=PAI&dq=Application of Muscle/Nerve Stimulation in Health and Disease&ots=CMV5rXiDQD&sig=Wg8u1YOC4PgvVDzcjdwBub5U2To (Accessed Jun. 2, 2011).
Wallwork et al., "The effect of chronic low back pain on size and contraction of the lumbar multifidus muscle," Manual Therapy, 14(5):496-500 (2009) available at: http://www.ncbi.nlm.nih.gov/pubmed/19027343.
Ward et al., "Architectural analysis and intraoperative measurements demonstrate the unique design of the multifidus for lumbar spine stability," J. Bone Joint Surg. [Am.] 91:176-185, PMC2663324 (2009).
Wikipedia, "Time-division multiplexing," https://en.wikipedia.org/wiki/Time-division_multiplexing (accessed Nov. 12, 2015).
Wright et al., "Morphologic and histochemical characteristics of skeletal muscle after long-term intramuscular electrical stimulation," Spine, 17(7):767-770 (1992) available at: http://www.ncbi.nlm.nih.gov/pubmed/1502640 (Accessed Aug. 2, 2011).
Written Opinion dated Feb. 3, 2014 in Int'l PCT Patent Appl. Serial No. PCT/US2012/070259.
Written Opinion dated Nov. 16, 2011 in Int'l PCT Patent Appl. Serial No. PCT/US2011/027934.
U.S. Appl. No. 15/202,435, filed Jul. 5, 2016, Beck et al.
U.S. Appl. No. 15/202,485, filed Jul. 5, 2016, Beck et al.
Medtronic Extension Passer 3555 Accessory Kit—Technical Instructions, 2 pages (2001).
Medtronic Interstim Therapy 3093 & 3889—Implant Manual, 38 pages (2010).
Medtronic Model 3464 Receiver/Extension Internalization Manual, SE-4 for Spinal Cord Stimulation (SCS), 7 pages (1986).
Medtronic Tunneling Rod Accessory Kit 8590-41—Technical Manual, 9 pages (No date available).
International Search Report & Written Opinion dated Sep. 28, 2017 in Int'l PCT Patent Appl. Serial No. PCT/IB2017/053945.
International Search Report & Written Opinion dated Oct. 20, 2017 in Int'l PCT Patent Appl. Serial No. PCT/IB2017/053946.
Deckers, et al., Chronic Low Back Pain: Restoration of Dynamic Stability, Nueromodulation, 18:478-486 (2015).

* cited by examiner

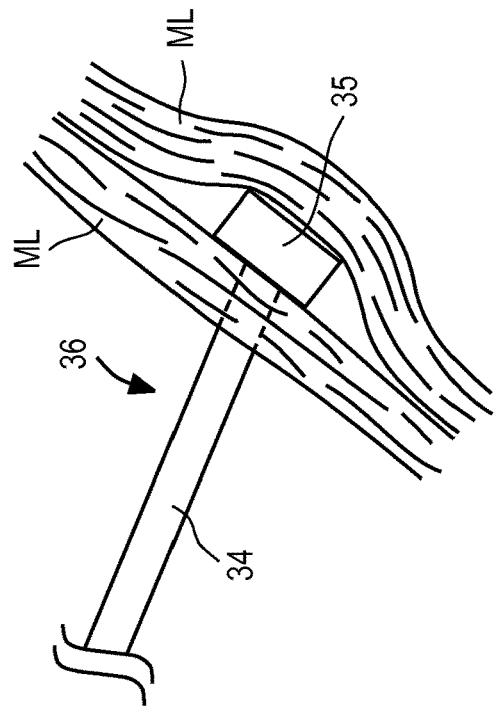
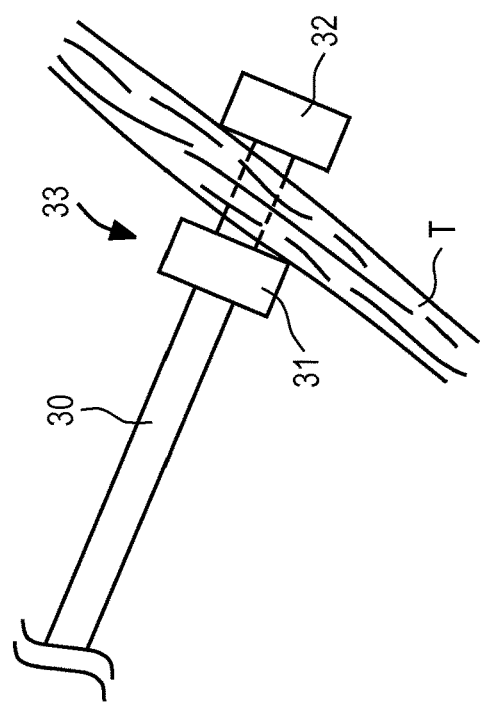
FIG. 3B
FIG. 3A

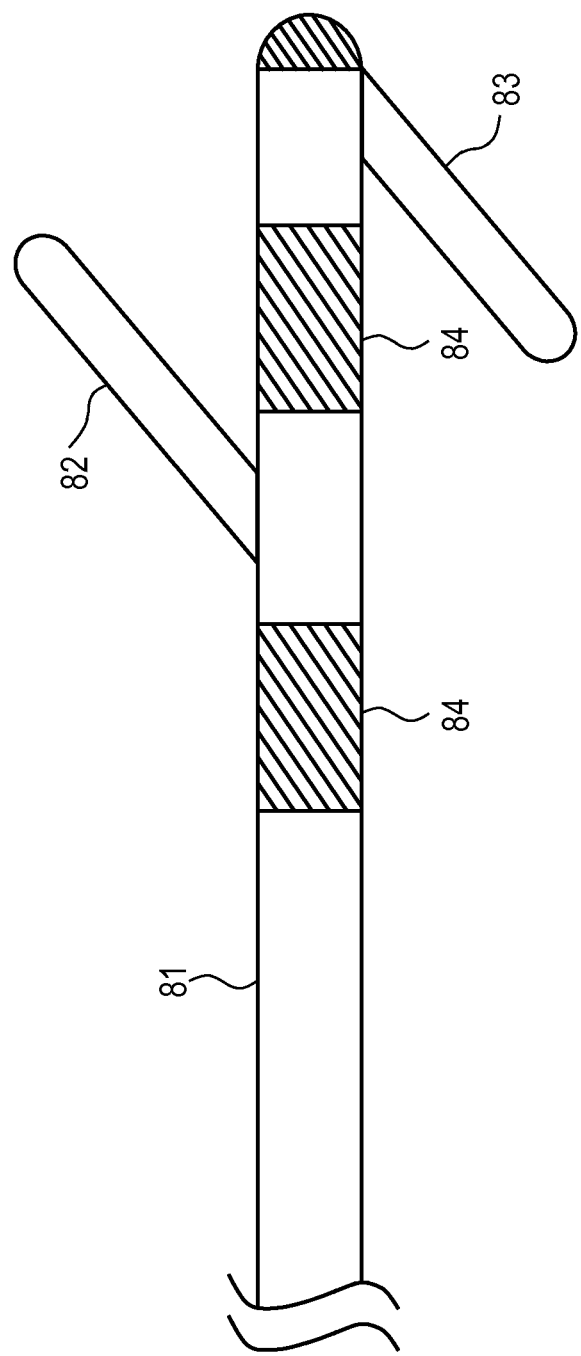

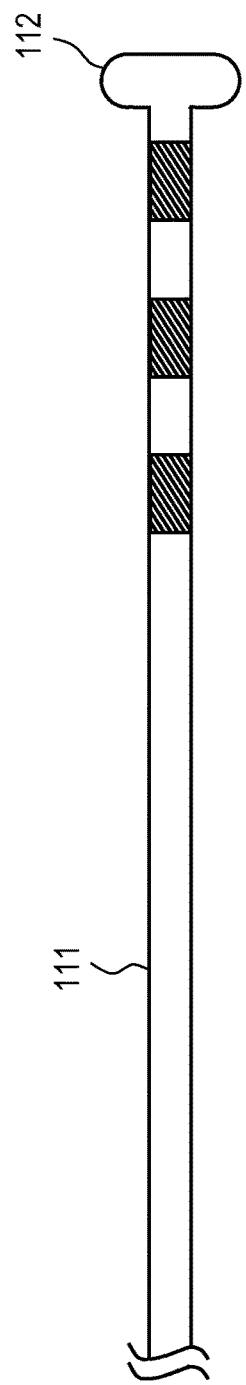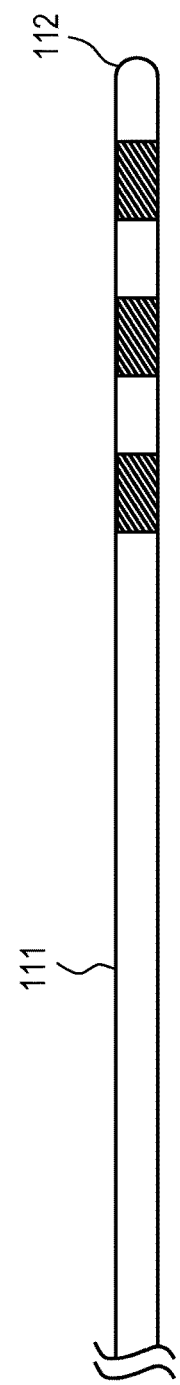

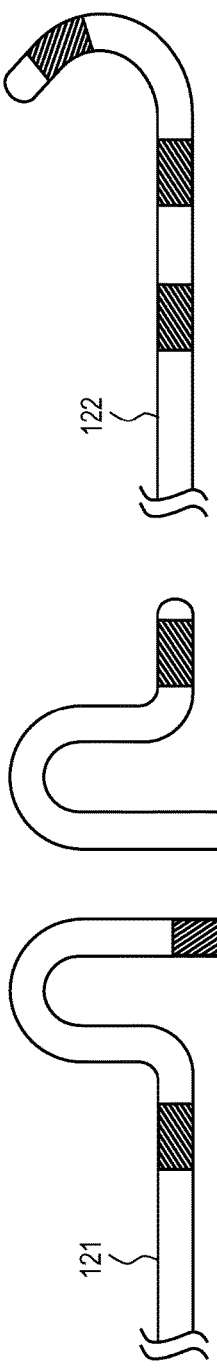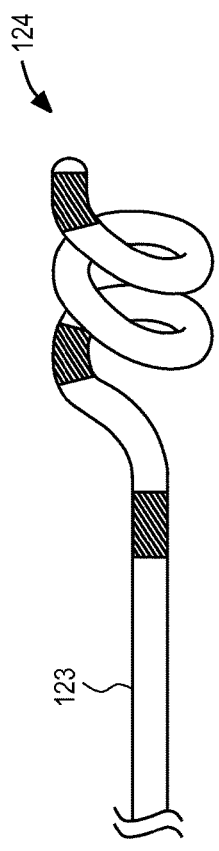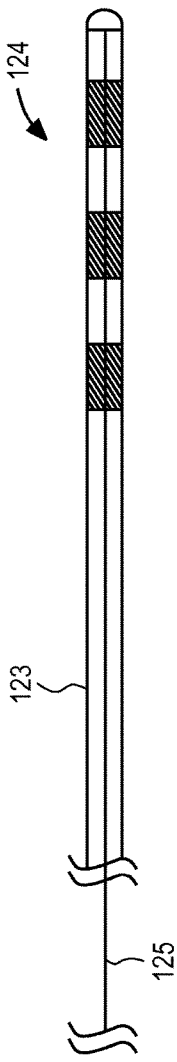

APPARATUS AND METHODS FOR ANCHORING ELECTRODE LEADS ADJACENT TO NERVOUS TISSUE

I. CROSS-REFERENCE TO RELATED APPLICATIONS

This application claims the benefit of priority of U.S. Provisional Application Ser. No. 61/659,334, filed Jun. 13, 2012.

II. FIELD OF THE INVENTION

This application generally relates to apparatus and methods for anchoring a medical device, such as an electrical stimulation lead, catheter or other generally elongated or tubular device in the body.

III. BACKGROUND OF THE INVENTION

Many medical devices incorporate an elongated or tubular element that is required to be positioned at a particular anatomical site. Such devices include pacemakers, spinal cord stimulators, peripheral nerve stimulators, and drug delivery catheters.

In the case of a pacemaker, for example, the leads may be threaded through a vein, and then anchored using a fixation element at the distal tip of the lead to prevent dislodgement. Such a fixation element may be a tine, fin, or screw that is secured in the trabeculae or muscle tissue of the ventricle.

Generally, it is desirable to implant and anchor a medical device using a minimally invasive approach, and for many devices, a percutaneous approach through a small incision is preferable. One drawback of a percutaneous approach is that relatively large and complex anchoring mechanisms cannot be deployed through the incision or using a needle, catheter, or cannula. Additionally, in many cases, there is no convenient anatomical structure to which the medical device may be anchored.

Sacral nerve stimulator leads may include a fixation element(s), such as a tine(s), projecting from the lead body to constrain movement of the lead body relative to the surrounding tissue. Tines on a sacral nerve lead, such as the InterStim™ lead available from Medtronic, Inc. of Fridley, Minn., generally are located at a substantial proximal distance from the electrodes and face in only one (proximal) direction. Such placement allows for relative movement of the electrodes as the muscle and connective tissue within which the tines are placed moves relative to the target of stimulation.

A spinal cord stimulator (SCS) may include an implantable pulse generator (IPG) connected to one or more leads having one or more electrodes configured to deliver electrical energy to the spinal cord to block pain signals from reaching the brain. Small changes in electrode position may in some cases adversely impact the system's ability to effectively deliver therapy. It may not be practical or feasible to provide an anchoring mechanism inside the spinal canal to anchor a lead of the SCS. The conventional technique for securing the lead is to stabilize the lead using a ligature sleeve or suture sleeve secured to the lead body and attached to the superficial fascia with a suture as described, for example, in U.S. Pat. No. 5,957,968 to Belden and U.S. Pat. No. 7,930,039 to Olson. This technique, while in common use, suffers from drawbacks including significant incidence of lead dislodgement. Another drawback is that the superficial tissue is often an undesirable distance from the target tissue of stimulation. Any change in patient posture which results in a change in the relative distance between the superficial fascia and the target tissue of stimulation results in tension being applied to the lead body and subsequent movement of the electrodes.

U.S. Patent Application Publication No. 2008/0228241 to Sachs and U.S. Patent Application Publication No. 2011/0224665 to Crosby et al., both assigned to the assignee of the present invention, and both incorporated herein in their entireties by reference, describe implanted electrical stimulation devices that are designed to restore neural drive and rehabilitate the multifidus muscle to improve stability of the spine. Rather than masking pain signals while the patient's spinal stability potentially undergoes further deterioration, the stimulator systems described in those applications are designed to reactivate the motor control system and/or strengthen the muscles that stabilize the spinal column, which in turn is expected to reduce persistent or recurrent pain. Sachs and Crosby also describe peripheral nerve stimulation, in which electrical energy is applied to a nerve to effect a physiological change, such as to elicit a muscle contraction or to block pain signals from traveling in the peripheral nerve.

While the stimulator systems described in the Sachs and Crosby applications seek to rehabilitate the multifidus and restore neural drive, use of those systems necessitates the implantation of one or more electrode leads in the vicinity of a predetermined anatomical site, such as the medial branch of the dorsal ramus of the spinal nerve to elicit contraction of the lumbar multifidus muscle. For that application, there is no convenient anatomical structure near the distal end of the lead to allow for use of a conventional anchoring mechanism on the lead. Anchoring the lead to the superficial fascia as described above may be effective in many cases, but may still be susceptible to the problems of dislodgement which may prevent proper therapy delivery.

The challenges of anchoring medical devices extend beyond electrical stimulation. For example, an intrathecal pump is a medical device configured to deliver small and metered amounts of a fluid containing a drug to target tissue, such as the spinal cord. The drug may be delivered by a small catheter that is placed inside the spinal canal, and the problems of dislodgement are similar to those described above. It would be desirable to provide a mechanism which more effectively anchors the catheter to prevent dislodgement and the possibility of the drug missing its intended target, or being delivered to an incorrect site.

U.S. Pat. No. 7,493,175 to Cates describes apparatus for subcutaneously anchoring a cardiac electrode lead using multiple tines. Such an apparatus would be undesirable for implantation in or adjacent to spinal muscle as the tines may become dislodged and tear the muscle during movement.

U.S. Pat. No. 7,797,053 to Atkinson describes a tether and a stent like device at the distal portion of a lead that may be expanded inside a cardiac vein to anchor a cardiac pacing lead. A similar stent-like anchor for a neurostimulation lead is described in U.S. Pat. No. 7,917,230 to Bly. U.S. Pat. No. 7,908,015 to Lazeroms describes a stimulation lead to be placed subcutaneously in which the fixation mechanism includes a movable mechanism at the distal end of the lead such that the lead diameter is increased at the distal end when engaged to provide anchoring. U.S. Pat. No. 8,170,690 to Morgan describes use of a helical element (screw) for anchoring a lead. These previously known anchoring systems are ill suited for neuromuscular stimulation because such systems have a high risk of dislodgement of the lead when implanted in or adjacent to muscle.

It would be desirable to provide electrode leads and methods of implantation wherein the lead is securely anchored within a patient, thus reducing the risk of dislodgement of the lead.

It further would be desirable to provide electrode leads and methods of implantation wherein an anchoring mechanism may be deployed using a percutaneous approach, a needle, a catheter, the lead itself, and/or a cannula.

IV. SUMMARY OF THE INVENTION

The present invention overcomes the drawbacks of previously-known by providing apparatus for neuromuscular electrical stimulation including an elongated member having a proximal region and a distal region, one or more electrodes disposed at the distal region of the elongated member, and first and/or second fixation elements disposed at the distal region of the elongated member. The first fixation element may be shaped and sized to contact, but not penetrate, tissue (e.g., a muscle, ligament, tendon, fascia) within a patient without damaging the tissue, so as to secure the one or more electrodes in or adjacent to a desired anatomical site within the patient. Also, the first and second fixation elements may be shaped and sized to sandwich or bracket tissue within a patient therebetween without damaging the tissue so as to secure the one or more electrodes in or adjacent to a desired anatomical site within a patient. Alternatively, at least one of the first or second fixation elements may be configured to be deployed between tissue layers (e.g., muscle layers) without damaging the tissue layers so as to secure the one or more electrodes in or adjacent to a desired anatomical site within a patient. The fixation elements may be configured to contact, but not penetrate tissue.

The one or more electrodes may be configured to be implanted in or adjacent to nervous tissue. A radiopaque marker(s) may be disposed at the distal region of the elongated member. For example, the radiopaque marker may be disposed on or within the first fixation element, the second fixation element, or both. The second fixation element may be a helical screw. Alternatively, the first fixation element may be angled distally or proximally relative to the elongated member and the second fixation element may be angled distally or proximally relative to the elongated member. The second fixation element may be disposed distally on the elongated member relative to the first fixation element and the second fixation element may be disposed at the distal end of the elongated member. The first and second fixation elements may be disposed on opposite sides of the elongated member relative to a longitudinal axis of the elongated member. The fixation elements may be expandable and/or extendable. The first and second fixation elements may be a flange, a partial flange, or a divided flange. The elongated member may have a groove and the first and/or second fixation elements may be partially disposed within the groove such that the first and/or second fixation elements rotate freely around the elongated member within the groove. The elongated member may have an elastic section that may be between the first and second fixation elements. The elongated member also may include a discontinuous portion at the distal region wherein the first fixation element is a coil exposed in the discontinuous portion. The apparatus may further include an implantable pulse generator and/or an implantable microstimulator coupled to the proximal region of the elongated member.

In accordance with yet another aspect of the present invention, a method of anchoring an elongated member having one or more electrodes for neuromuscular electrical stimulation is provided. The method may include providing an elongated member having a fixation element disposed at a distal region of the elongated member and inserting the fixation element against or between tissue layers (e.g., muscle layers) without damaging the tissue layers so as to secure the one or more electrodes in or adjacent to a desired anatomical site within a patient.

The one or more electrodes may be secured in or adjacent to nervous tissue, e.g., the medial branch of the dorsal rami. The method may further include delivering electrical energy to the dorsal rami or other nervous tissue with the one or more electrodes.

V. BRIEF DESCRIPTION OF THE DRAWINGS

FIGS. 3A and 3B depict exemplary embodiments for bidirectional stabilization of a medical device.

FIG. 8 shows the distal region of an exemplary electrode lead having first and second fixation elements that are each single projections opposed to each other in both direction as well as being on opposite sides of the lead body.

FIGS. 11A and 11B show the distal region of an exemplary electrode lead having an expandable fixation element, wherein the fixation element is expanded in FIG. 11A and contracted in FIG. 11B.

FIGS. 12A through 12C show the distal region of exemplary electrode leads in the deployed state having a flexible shape for anchoring the lead, wherein FIG. 12A shows a serpentine shape, FIG. 12B shows a J-shape, and FIG. 12C shows a spiral shape.

FIG. 12D depicts the electrode lead of FIG. 12C in a delivery state.

VI. DETAILED DESCRIPTION OF THE INVENTION

The present invention is directed to methods and apparatus for anchoring electrode leads suitable for use with an implantable neuromuscular electrical stimulation ("NMES") device, such as described in the above-incorporated U.S. Patent Application Publication Nos. 2008/0228241 to Sachs and 2011/0224665 to Crosby. The devices described in those applications supply electrical pulses to nerves innervating the spinal muscles, such as the multifidus muscles, and stimulate the nerves controlling those muscles to effect a therapy designed to restore neural control and rehabilitation of the muscle. The implantable stimulator is disposed subcutaneously, and is coupled to one or more electrode leads having electrodes in contact with the target muscle, or nerves innervating the target muscles, or other anatomical structures associated with the muscle, such as ligaments and tendons. The NMES stimulation supplied by the stimulator applies a pulse regime that is very different than those employed by previously-known Spinal Cord Stimulation or Peripheral Nerve Stimulation therapy devices, where the goal of the stimulation is simply to reduce or block the transmission of pain signals to the patient's brain, rather than reactivate the motor control system and/or rehabilitate the muscle.

Conventional anchoring mechanisms are ill suited for anchoring NMES electrode leads to muscle and/or between muscle layers, especially to spinal muscles, because such muscles are mobile creating high risks of lead dislodgement and muscle damage. Accordingly, the present invention is directed toward anchoring stimulation leads into an anatomical structure, e.g., tissue such as muscle, with at least one fixation element using either minimally invasive or percutaneous techniques. Advantageously, the fixation element(s) are sized and shaped to secure the lead to muscle without damaging the muscle such that one or more electrodes are positioned in or adjacent to a desired anatomical site, e.g., nervous tissue, within a patient. Such fixation elements may be a flange, a partial flange, or a divided flange optionally having a flat and/or smooth surface configured to minimize muscle damage/tear. The fixation elements provide bidirectional stabilization for the electrode lead and may or may not be angled relative to the lead.

Figure 1:
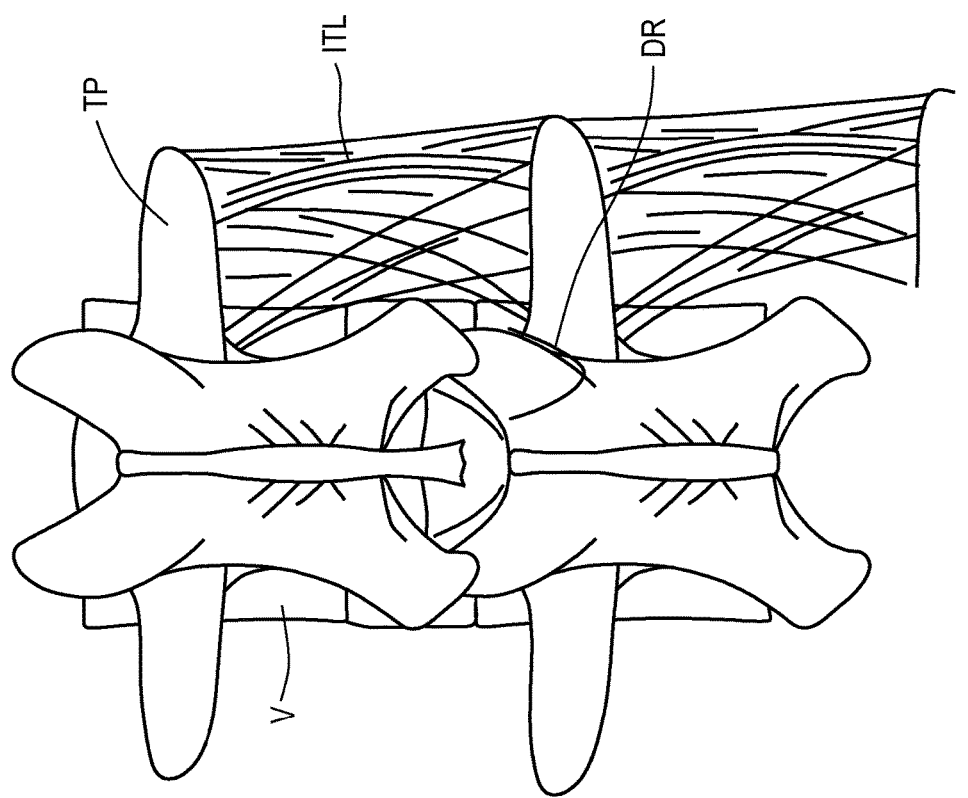
FIG. 1 shows an anterior-posterior view of two lumbar vertebrae, including the inter-transverse ligament and surrounding tissue.
Figure 2:
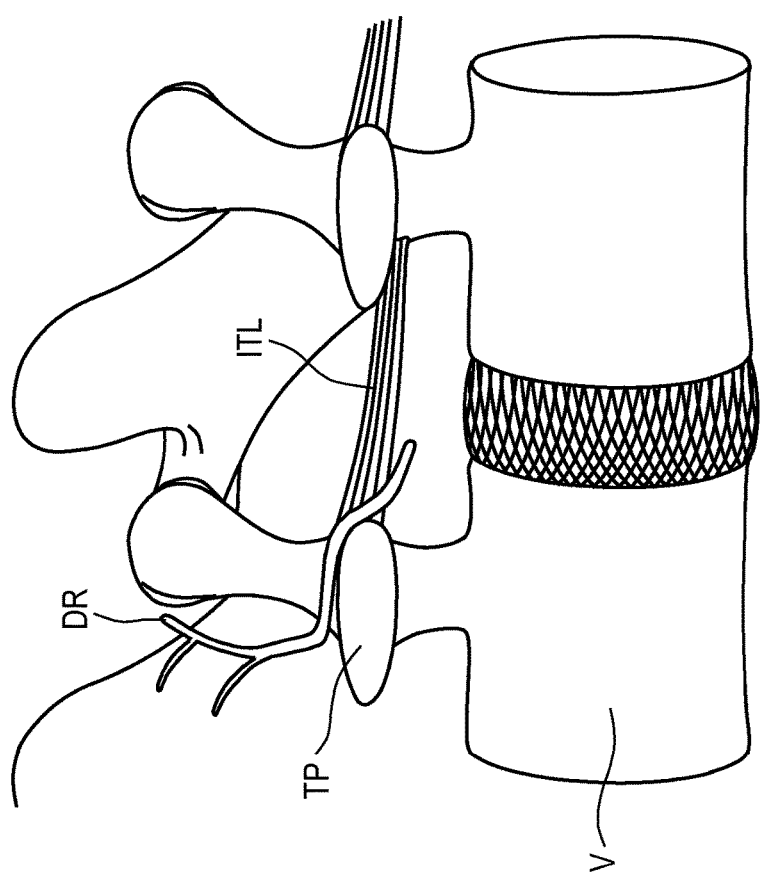
FIG. 2 shows a lateral view of two lumbar vertebrae, including the inter-transverse ligament and surrounding tissue.

FIG. 1 and FIG. 2 show anterior-posterior projection and lateral projection, respectively, of a segment of a typical human lumbar spine having a vertebral body V, transverse process TP, inter-transverse ligament ITL, and a dorsal rami DR. As described herein, an apparatus of the present invention, such as an electrode lead, may be anchored so as to secure the apparatus in or adjacent to a desired anatomical structure, e.g., nervous tissue. In one embodiment, the apparatus is anchored in or adjacent to the medial branch of the dorsal rami DR such that electrodes may stimulate the medial branch of the dorsal rami DR.

FIGS. 3A and 3B illustrate bidirectional stabilization of a medical device in accordance with aspects of the present invention. In FIG. 3A, the medical device includes elongated member 30 having first fixation element 31 and second fixation element 32 disposed at distal region 33 of elongated member 30. First and second fixation elements 31 and 32 are shaped and sized to sandwich or bracket tissue T (e.g., a muscle, ligament, tendon, fascia, or other suitable tissue) therebetween without damaging the tissue T. Such fixation elements may be a flange, a partial flange, or a divided flange optionally having a flat and/or smooth surface configured to minimize muscle damage/tear. First fixation element 31 may be configured to resist displacement in a first direction (e.g., advancement) and second fixation element 32 may be configured to resist displacement in a second direction (e.g., retraction). Illustratively, second fixation element 32 is disposed distally on elongated member 30 relative to first fixation element 31 and second fixation element 32 may be disposed at the distal end of elongated member 30.

FIG. 3B shows an alternative embodiment of the medical device of the present invention, wherein elongated body 34 and fixation element 35 are disposed at the distal region 36 of elongated body 34. The lead body is stabilized by deployment of fixation element 35 configured to resist displacement bidirectionally within a tissue plane or between two discrete tissue planes, e.g., muscle layers ML.

Figure 4:
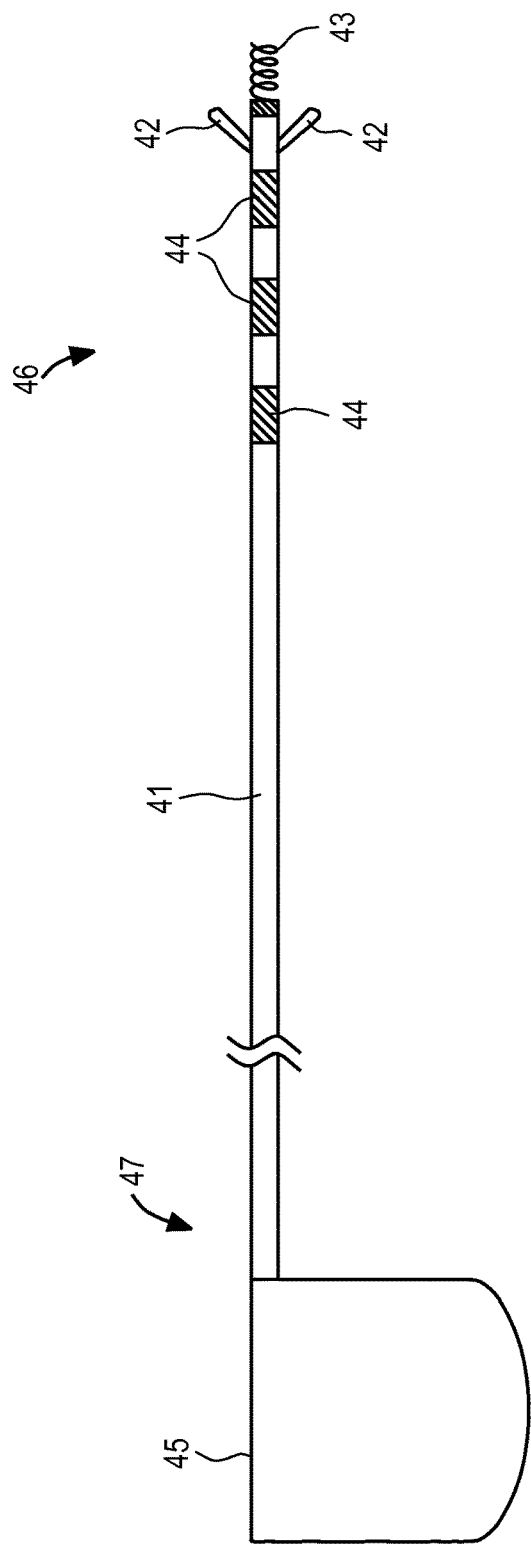
FIG. 4 shows an exemplary electrode lead having a distal helical screw and a fixation element.

FIG. 4 illustrates an exemplary apparatus for neuromuscular electrical stimulation having an electrode lead constructed in accordance with the principles of the present invention. Apparatus 40 includes elongated member 41 having fixation elements 42, helical screw 43, electrodes 44, and implantable pulse generator (IPG) 45. Fixation elements 42, helical screw 43, and electrodes 44 are disposed at distal region 46 of elongated device 41. Fixation elements 42 are sized and shaped to secure electrodes in or adjacent to a desired anatomical site. Fixation elements 42 may comprise a polymer, metal or ceramic, and are configured to resist motion in a first direction and prevent, in the case illustrated, excessive distal advancement of the apparatus, as well as migration distally. Helical screw 43 is configured to secure elongated member 41 to an anatomical structure and may configured to engage tissue immediately distal to the elongated member 41 forming a mechanical lock preventing movement in a second direction. Helical screw 43 may be anchored to the tissue by rotation of elongated member 41 or by deployment of a mechanism in which the screw rotates relative to elongated member 41, as is known in the art of cardiac leads. While the apparatus illustratively includes helical screw 43, it should be understood that a barb, hook, or the like may be used may also serve as one of the electrodes. Electrodes 44 are configured to deliver electrical energy and may be stimulation electrodes known in the art. Elongated member 41 (e.g., a lead) illustratively includes three electrodes 44, although the scope of the disclosure is not limited thereto.

IPG 45 is disposed at proximal region 47 of elongated member 41. IPG 45 is operatively coupled to electrodes 44 and is configured to direct electrodes 44 to deliver electrical energy. IPG 45 may be coupled to electrodes 44 via a lead. Alternatively, electrodes may be incorporated into an implantable microstimulator without a lead, as described below. IPG 45 may include may comprise a commercially available microcontroller unit including a programmable microprocessor, volatile memory, nonvolatile memory such as EEPROM for storing programming, and nonvolatile storage, e.g., Flash memory, for storing a log of system operational parameters and patient data. As will be appreciated by one of ordinary skill in the art, while IPG 45 is illustratively implantable, the pulse generator may be disposed external to a body of a patient on a temporary or permanent basis without departing from the scope of the present invention. In such an embodiment, the pulse generator may be coupled to the electrodes by percutaneous leads. Alternatively, the pulse generator and the electrodes may be completely external such that the leads are applied to the skin over a suitable location to elicit muscle contraction.

Figure 5:
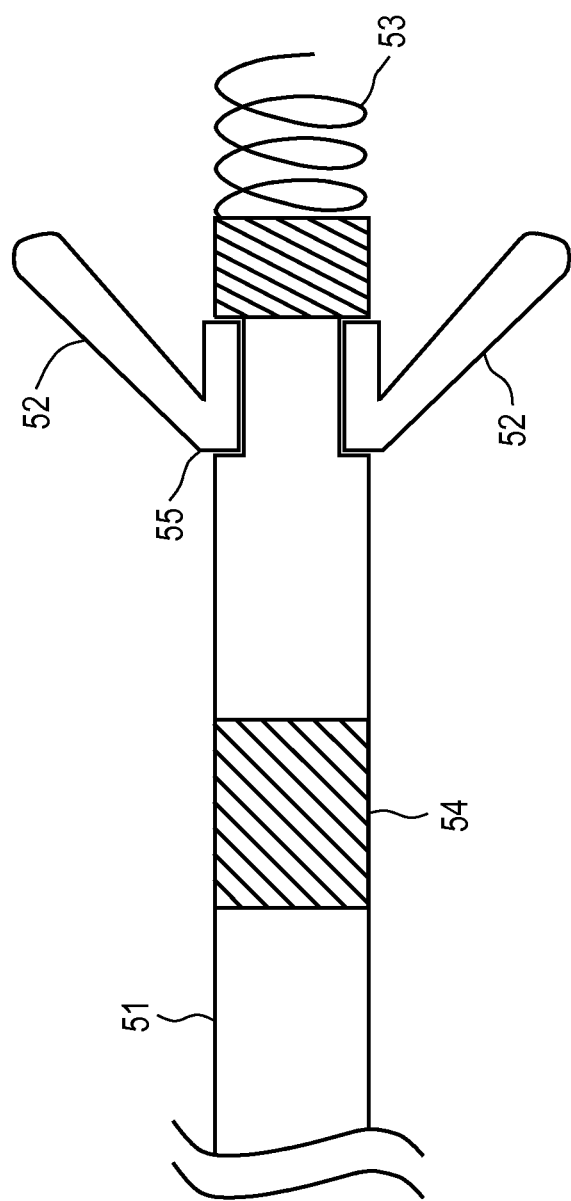
FIG. 5 illustrates the distal region of an alternative electrode lead having a distal helical screw and a fixation element.

FIG. 5 illustrates the distal region of an exemplary electrode lead having elongated member 51, fixation elements 52, helical screw 53, and electrode 54. Fixation elements 52 are disposed within groove 55 of elongated member 51 such that fixation elements 52 are free to rotate with respect to elongated member 51 and electrode 54. Such a configuration allows for deployment of the helical screw 53 without the risk of fixation elements 52 impeding rotation or becoming undesirably entangled in a structure such as a nerve during rotation.

Figure 6:
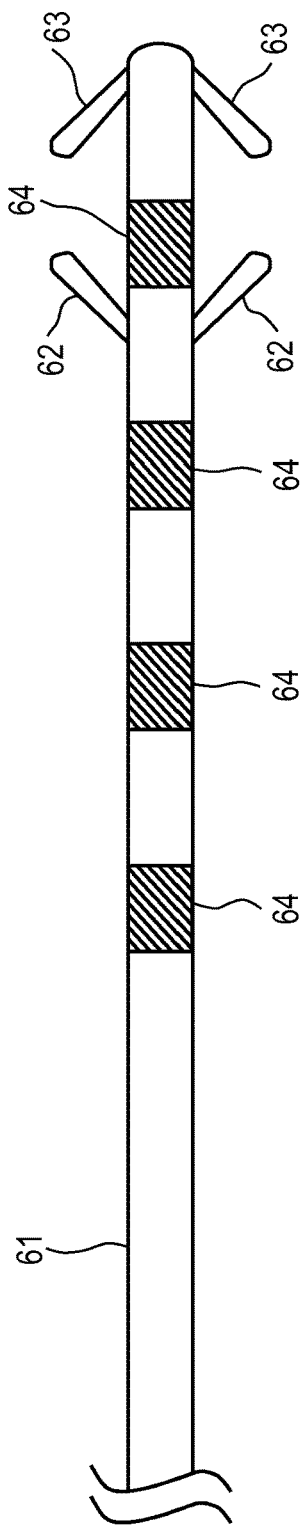
FIG. 6 shows the distal region of an exemplary electrode lead having first and second fixation elements employed in opposing directions to obtain bidirectional stabilization.

FIG. 6 illustrates the distal region of an exemplary electrode lead having elongated member 61, first fixation elements 62, second fixation elements 63, and electrodes 64. First fixation elements 62 are angled distally relative to elongated member 61, and resist motion in the first direction and prevent, in the case illustrated, insertion of the lead too far, as well as migration distally. Second fixation elements 63 are angled proximally relative to elongated member 61 and penetrate through a tissue plane and deploy on the distal side of the tissue immediately adjacent to the target of stimulation. First fixation elements 62 are configured to resist motion in the opposite direction relative to second fixation elements 63. This combination prevents migration both proximally and distally, and also in rotation. The spacing between the fixation elements is defined by the structure around which they are to be placed. In one embodiment, the spacing is between 2 mm and 10 mm.

Figure 7C:
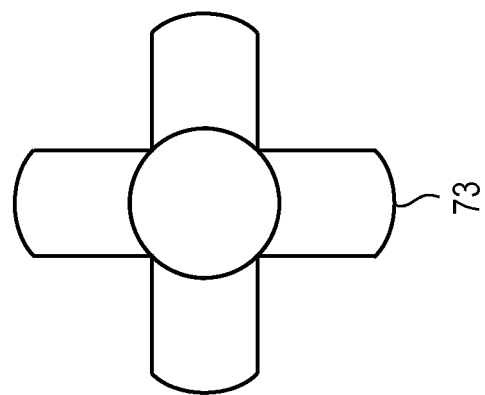
FIGS. 7A through 7C depict cross sectional views of a number of possible fixation element configurations.
Figure 7B:
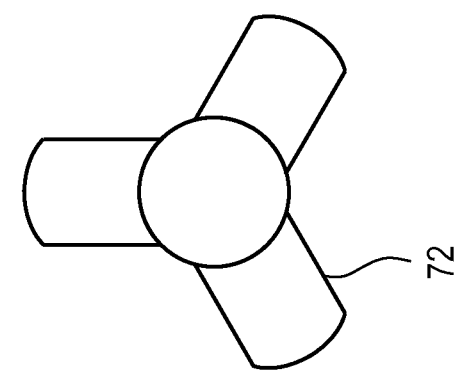
Figure 7A:
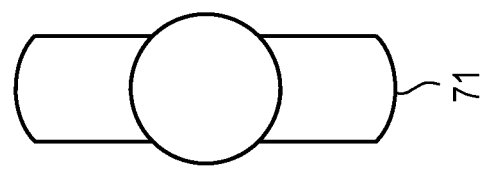

FIGS. 7A through 7C illustrate exemplary fixation element configurations in accordance with the principles of the present invention. The fixation elements may be made, for example, of a polymer, metal and/or ceramic. The fixation elements may be a flange, a partial flange, or a divided flange optionally having a flat and/or smooth surface configured to minimize muscle damage/tear. The fixation elements provide bidirectional stabilization for the electrode lead and may or may not be angled relative to the lead. Fixation elements may include any number of projections, generally between 1 and 8. FIGS. 7A, 7B, and 7C illustrate a medical device wherein the fixation element with two projections 71, three projections 72 and four projections 73, respectively. In one embodiment, the length of each projection is between 1 mm and 5 mm and the width is between 0.25 mm and 2 mm.

Based on the anatomical structures adjacent to the target of stimulation and the available access to approach said structures, it may be desirable to orient the fixation elements such that they minimize the size of the structure needed in order to achieve suitable placement. FIG. 8 illustrates the distal region of an electrode lead having elongated member 81, first fixation element 82 angled distally, second fixation element 83 angled proximally, and electrodes 84.

Figure 9:
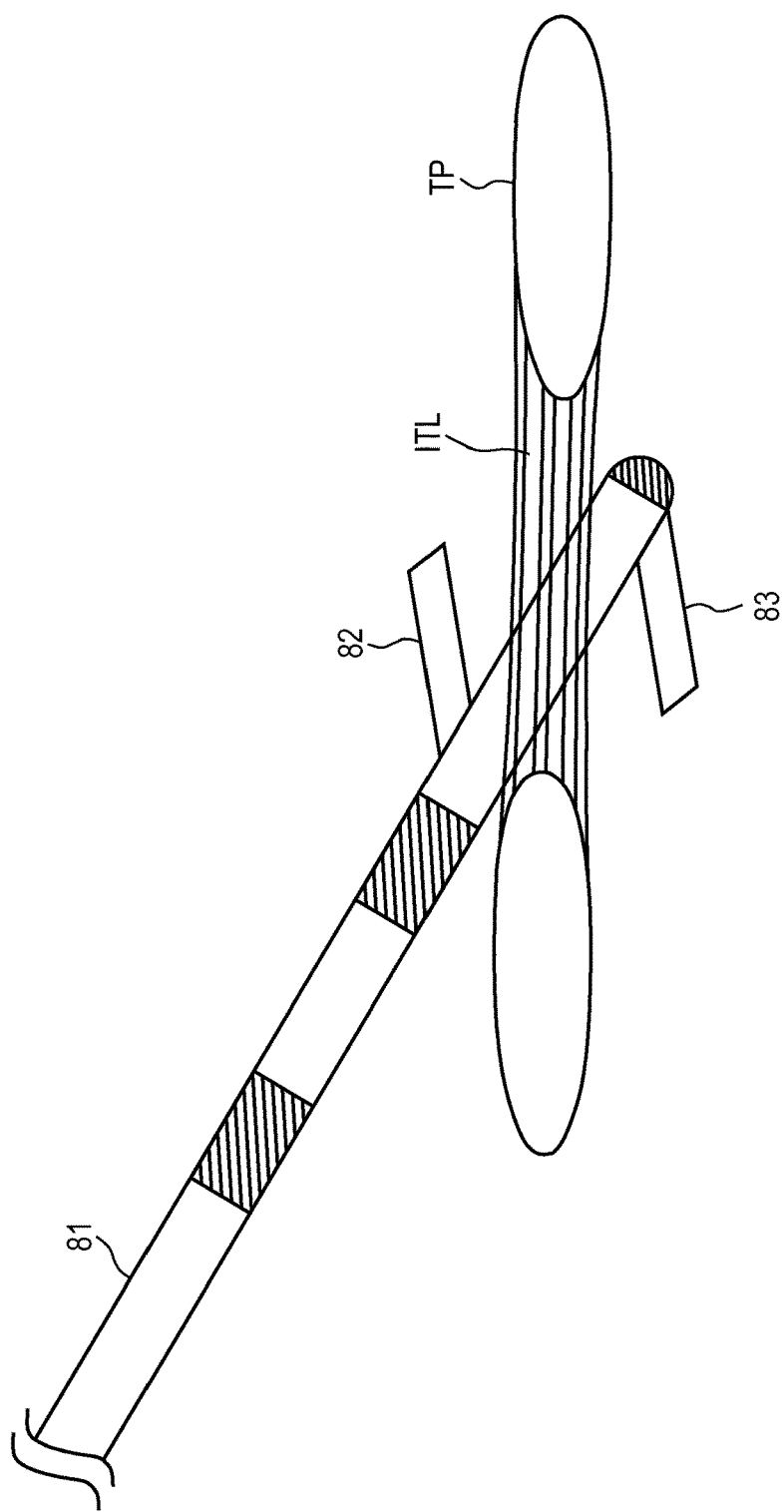
FIG. 9 shows the electrode lead of FIG. 8 placed with the tissue surrounding the inter-transverse ligament.

FIG. 9 shows the electrode lead of FIG. 8 placed around the tissue surrounding the inter-transverse ligament ITL for stimulating the medial branch. In this configuration, during lead placement elongated member 81 may be rotated so as to orient fixation elements 82 and 83 relative to the inter-transverse ligament ITL, which lies parallel to the spine between adjacent transverse processes TP.

Figure 10:
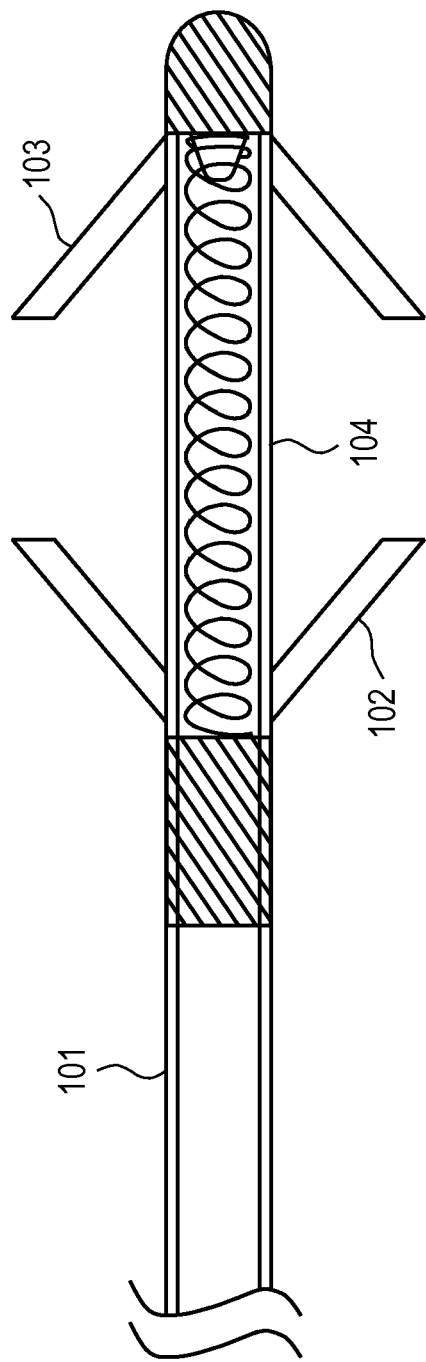
FIG. 10 shows the distal region of an exemplary electrode lead having opposing fixation elements wherein the lead located between the fixation elements is configured to be temporarily elongated.

FIG. 10 illustrates the distal region of an exemplary electrode lead having elongated member 101, first fixation element 102, second fixation element 103, and elastic portion 104. Elastic portion 104 is substantially more elastic than the main structure of the elongated member 101 to allow for penetration of the intended anatomic structure and deployment of first fixation element 102 on the distal side of the structure. Once achieved, axial tension applied proximally causes elongation of elastic portion 104 up to the point that second fixation element may deploy on the proximal side of the intended anatomic structure. This configuration permits placement of a single design within anatomical structures of different thicknesses. Elastic portion 104 would be capable of elongating up to 300% of its natural length and subsequently return to that natural length after the loading is removed. The elasticity may be achieved through the selection of lower durometer polymers with suitable elastic properties, or by incorporation of a super-elastic spring made of a material such as nitinol.

FIGS. 11A and 11B illustrate the distal region of an another exemplary electrode lead having elongated member 111 and expandable fixation element 112. Expandable fixation element 112 has a significantly larger diameter than elongated member 111 in an expanded state. FIG. 11A shows expandable fixation element 112 in the expanded state and FIG. 11B shows expandable fixation element 112 in a contracted state. In one embodiment, expandable fixation element 112 is contracted using a vacuum coupled to the proximal end of elongated member 111 permitting placement via standard techniques. Once the distal end of elongated member 111 is passed through the intended structure, the vacuum is removed and expandable fixation element 112 returns to its original size as shown in FIG. 11A. This arrangement overcomes the challenges typically associated with expanding a structure such as a balloon for fixation in that a typical balloon requires constant pressure to remain inflated. The adoption of a vacuum to reduce diameter as opposed to using positive pressure to increase diameter effectively ameliorates the concerns of chronic stability in these types of structures.

FIGS. 12A through 12C show the distal region of exemplary electrode leads in the deployed state having a flexible shape for anchoring the lead, wherein FIG. 12A shows a serpentine shape electrode lead 121, FIG. 12B shows a J-shape electrode lead 122, and FIG. 12C shows a spiral shape electrode lead 123. This shape may be achieved by prefabricating the lead body in the desired shape, or incorporating a component that retains this shape, or both. That shape may be three dimensional or two dimensional in nature and may be of consistent pitch or variable pitch. This shape may be straightened via the insertion of a stylet or other stiffening element during lead placement, and then the lead body will relax into the anchor shape in the absence of the stiffening element.

Figure 13:
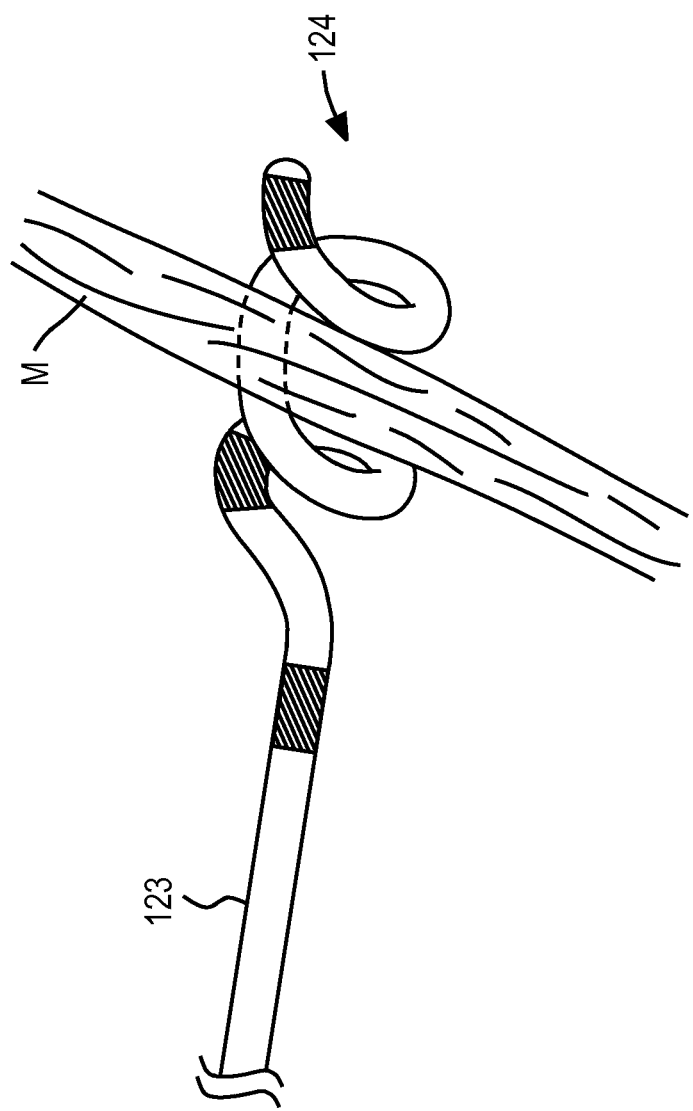
FIG. 13 shows the electrode lead of FIG. 12C deployed at tissue immediately surrounding the inter-transverse ligament.

FIG. 12D depicts the electrode lead of FIG. 12C in a delivery state. Introduction of a wire 125, such as a stylet, causes distal end 124 to straighten. Lead 123 then may be placed in the desired location. After placement, wire 125 is removed and distal end 124 returns to its natural state, engaging the desired anatomical structure, illustratively muscle M, and providing stabilization in both a first and a second direction as shown in FIG. 13.

Figure 14:
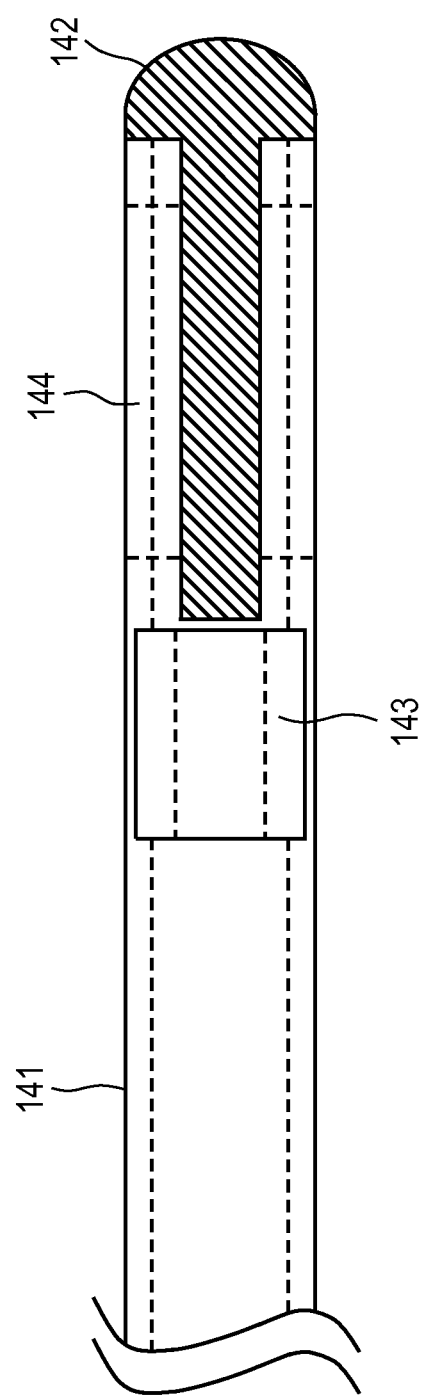
FIG. 14 shows the distal region of an exemplary electrode lead having an expandable fixation element in a delivery state.
Figure 15:
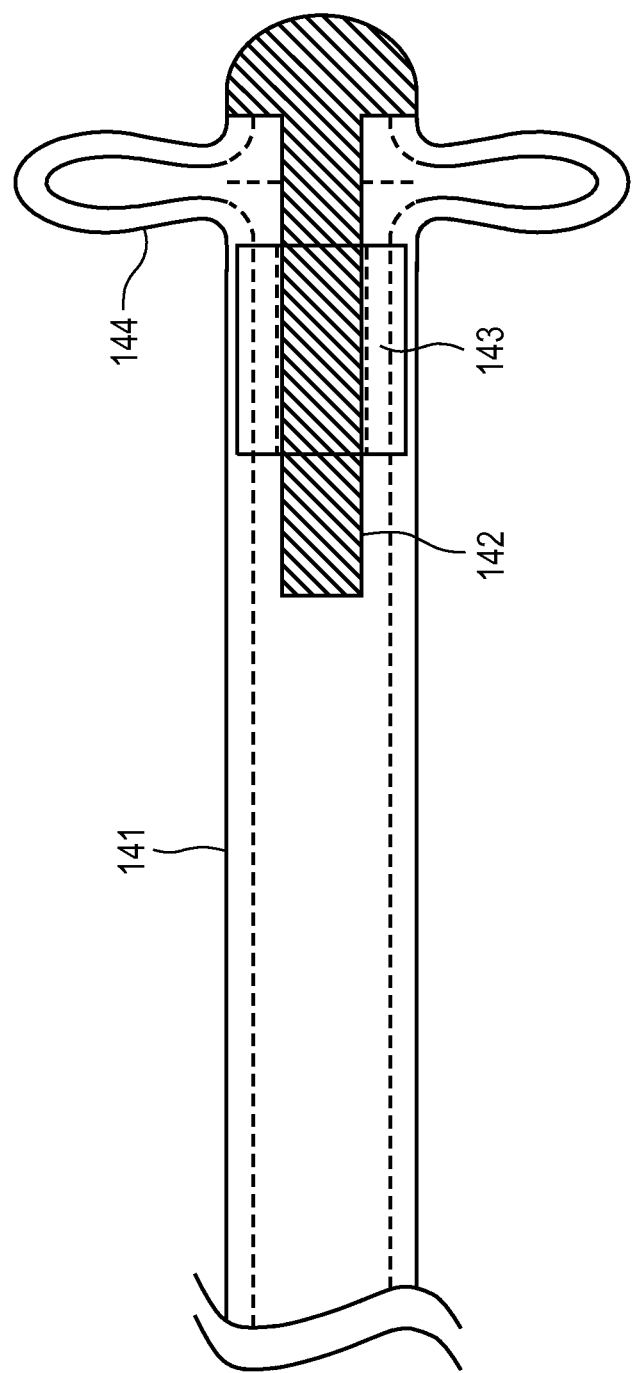
FIG. 15 shows the electrode lead of FIG. 14 having the fixation element expanded in the deployed state.

The present invention further provides embodiments for deploying fixation elements actively as shown in FIGS. 14 and 15. FIG. 14 depicts the distal region an exemplary electrode lead having an expandable fixation element shown in a delivery state. The electrode lead includes elongated member 141, cap 142, nut 143, and expandable fixation element 144. Cap 142 is disposed at the distal end of elongated member 141. The proximal end of cap 142 interfaces with nut 143, also joined to elongated member 141, but more proximally. Between cap 142 and nut 143, elongated member 141 is slit allowing expandable fixation element 144 to deform in a predictable manner. Upon deployment of the electrode lead, cap 142 is driven proximally through nut 143 within elongated member 141. This effectively shortens the distance between the joining points of 142 and 143 to elongated member 141 resulting in a bulging of expandable fixation element 144. These protrusions may be located such that the provide stabilization within a tissue plane or between two adjacent tissue planes.

Figure 16:
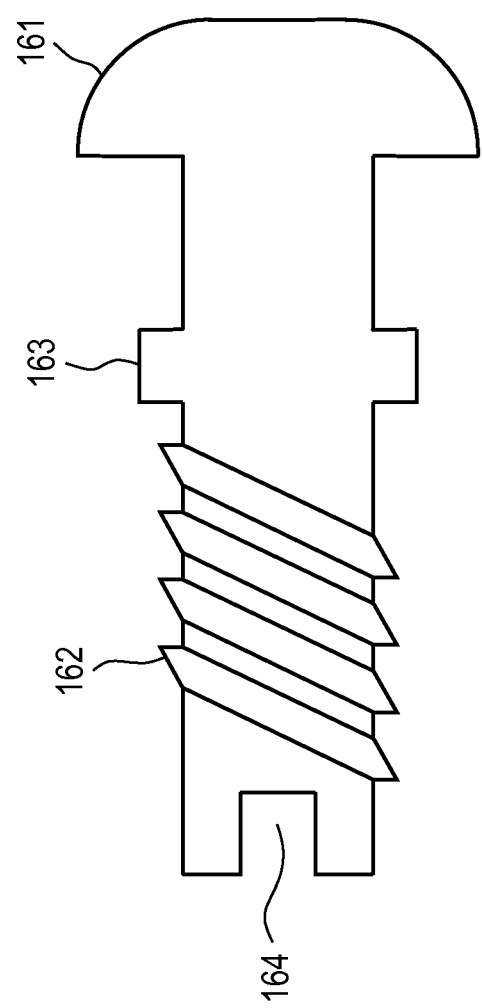
FIG. 16 shows an exemplary threaded cap that may be used in the electrode lead of FIG. 14.

FIG. 16 illustrates an exemplary cap for use in the electrode lead of FIG. 14. Cap 161 includes external threads 162, stopper 163, and opening 164. Threads are configured to mate with threads on the nut of FIG. 14. Rotation of cap 161 within the nut drives the two together resulting in deployment. Opening 164 at the distal end of cap 161 is configured to accept a stylet fitted with an end designed to mate with 164 and allow transmission of torque. Cap 161 may also incorporate stopper 163 designed to prevent excessive deployment and to secure the position of the two components relative to each other.

Figure 17:
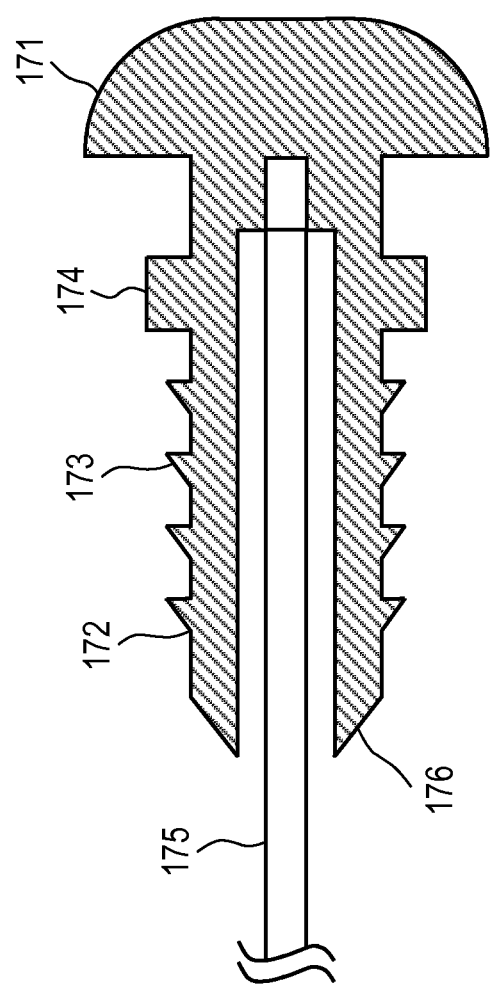
FIG. 17 shows an exemplary ratcheting cap that may be used in the electrode lead of FIG. 14.

FIG. 17 illustrates an alternative cap for use in the electrode lead of FIG. 14. Cap 171 includes cantilevered arms 172 that incorporate linearly arranged external teeth 173 configured to mate with internal teeth on the nut. Wire 175 is engaged into cap 171 allowing wire 175 to be pulled proximally into the nut locking the two together via the meshed teeth. Alternatively, wire 175 may be a pre-installed length of suture which is used to bring the two components together via counter traction. The excess length of suture would then be trimmed and placed inside the device header. This mechanism may be removed by insertion of a stylet which incorporates a distal feature that mates with the leading edge bevel 176 of cantilevered arms 172. Pressure applied inwards on arms 172 would disengage the teeth and allow cap 171 to move distally.

Figure 18:
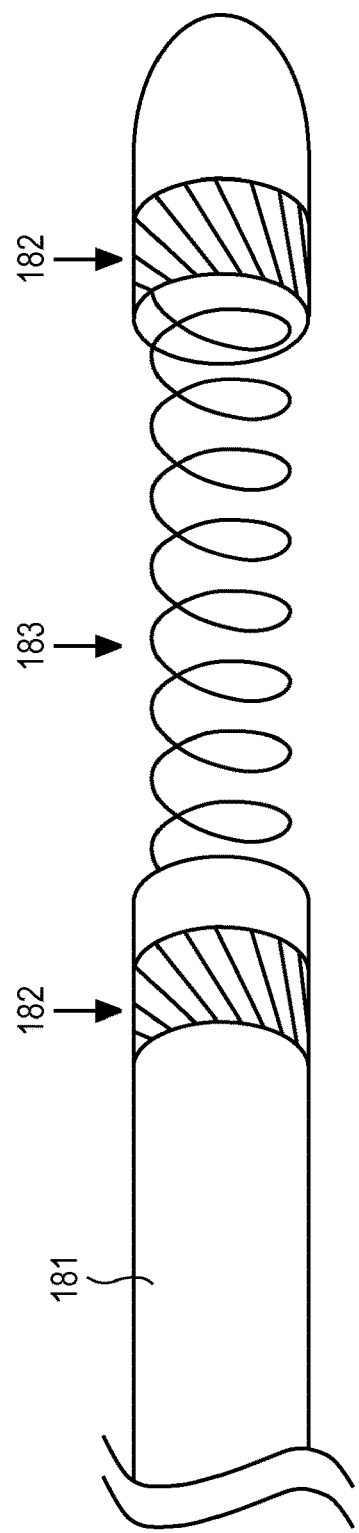
FIG. 18 illustrates the distal region of an exemplary electrode lead having an exposed fixation element to allow for tissue ingrowth.

FIG. 18 illustrates the distal region of an exemplary electrode lead having elongated member 181, electrodes 182, and fixation element 183. Illustratively, one electrode 182 is disposed distal to fixation element 183 and another electrode 182 is disposed proximal fixation element 183 although, as will be understood by one of ordinary skill in the art, the scope of the invention is not limited thereto. Fixation element 183 may be a conductor coil of at least one insulated wire coupled to distal electrode(s) 182. The wire may be cowound with one or more other conductors which connect to other electrodes 182 in elongated member 181, and the wires may be enclosed in elongated member 181 insulating tubing for most of its length. The leads are connected to the IPG with a demountable connector or permanently with a typical construction well known to one familiar with the art. As illustrated, fixation element 183 may be exposed for a portion of its length, for example between electrodes 182, where a portion of elongated member 181 is discontinuous. The exposed coil section provides a scaffolding for tissue ingrowth (such as scar tissue), and the tissue ingrowth reduces risk of or prevents movement of electrodes 182. During the acute phase (before tissue ingrowth), the geometry of the exposed electrode (e.g., non-smooth sides) provides sufficient anchoring to reduce the risk of or prevent dislodgement or movement of the lead. During implantation, a locking stylet of construction well known to one of ordinary skill in the art may be used to lock to at least one of the electrodes 182 to provide structural strength during the surgical procedure. Advantageously, elongated member 181, leads, and fixation element 183 are isodiametric, allowing implantation and straightforward re-positioning with a percutaneous technique through a needle or introducer. The lead may be removed by using a locking stylet which engages with at least one of electrodes 182, thus providing structural strength. Alternatively, the lead my be removed by sliding a catheter over the outside of the lead along its entire length which is enabled by the fact that the lead body is isodiametric.

Figure 19:
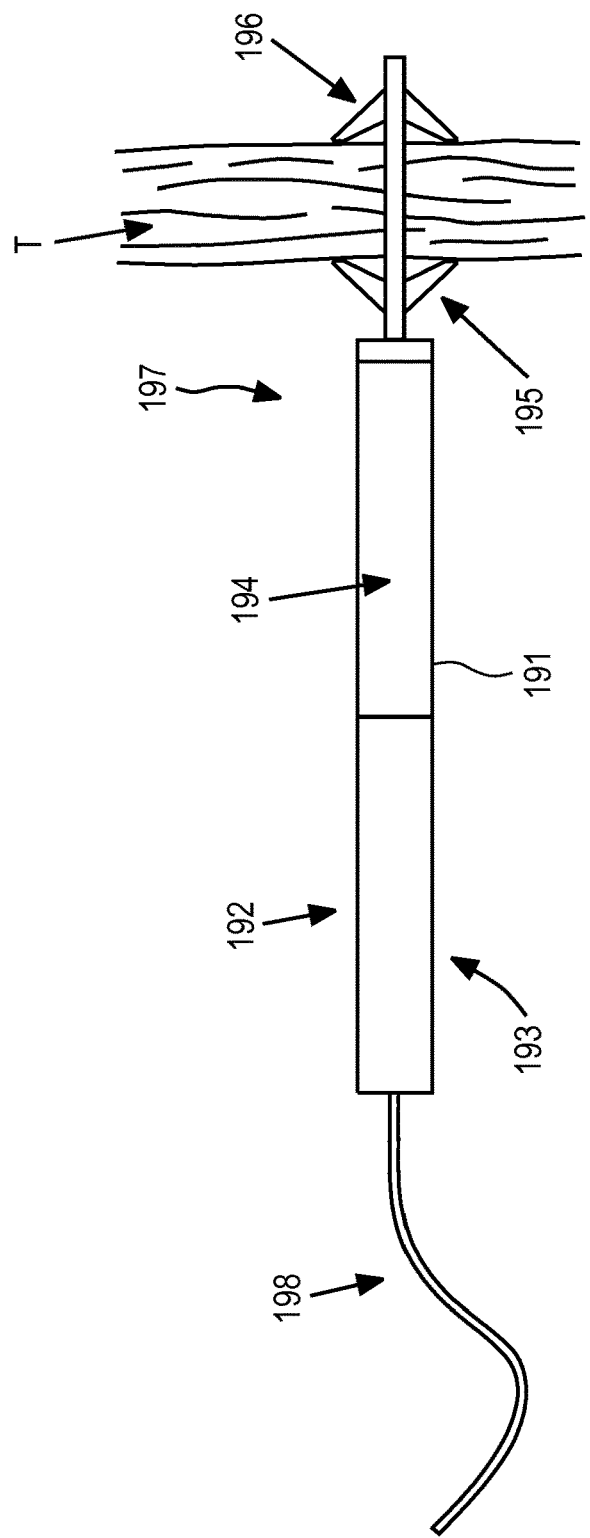
FIG. 19 shows an exemplary implantable microstimulator coupled to an electrode and fixation elements of the present invention.

FIG. 19 shows another aspect of the present invention wherein the fixation element(s) and electrode(s) are coupled to an implantable microstimulator. Illustratively, the device includes elongated member 191 coupled to microstimulator 192 at proximal region 193, and electrode 194, first fixation element 195, and second fixation element 196 at distal region 197. Microstimulator 192 is operatively coupled to electrode 194 and is configured to direct electrode 194 to deliver electrical energy. Microstimulator 192 may be configured similarly to stimulators described in, for example, U.S. Pat. No. 6,735,474 to Loeb or U.S. Patent Application Publication No. 2012/0283800 to Perryman. Microstimulator 192 may be injectable, surgically placed, or placed percutaneously, and may be internally powered or externally powered, e.g., via an external power source that transmits power to microstimulator 192 by radio frequency (RF) or microwaves. Microstimulator 192 may be secured to tissue T (e.g., a muscle, ligament, tendon, fascia, or other suitable tissue) such that one or more electrodes 194 are disposed in or adjacent to a desired anatomical site within the patient. Illustratively, the device may be anchored using first and second fixation elements 195, 196 similar to first and second fixation elements 62 and 63 of FIG. 6. However, as will be understood by one of ordinary skill in the art, fixation elements 31, 32 (FIG. 3A), 35 (FIG. 3B), 42, 43 (FIG. 4), 52, 53 with groove 55 (FIG. 5), 82, 83 (FIG. 8), 102, 103 with elastic portion 104 (FIG. 10), 112, (FIGS. 11A-11B), 144 (FIG. 14), and/or 183 (FIG. 18) may be coupled to an implantable microstimulator without departing from the scope of the present invention.

In FIG. 19, illustratively, first fixation element 195 is disposed proximal to tissue T to reduce the risk of or prevent further advancement through the tissue plane, and second fixation element 196 is disposed distal to tissue T to reduce the risk of or prevent retraction (dislodgement) of microstimulator 192 and electrode 194.

Pigtail 198 may be removably coupled to microstimulator stimulator. Pigtail 198 also may include one or more electrodes disposed along its length to provide flexibility in choice of stimulation configuration or parameters. In one embodiment, first and second fixation elements 195, 196 are coupled to pigtail 198. In such an embodiment, elongated member 191, microstimulator 192, and electrode 194 have a lumen therethrough longitudinally such that pigtail 198 may pass through the lumen. In operation, pigtail 198 having first and second fixation elements 195, 196 is advanced to tissue T by a delivery mechanism (e.g., a guidewire, needle, stylet or the like) and first and second fixation elements 195, 196 are secured to tissue T. Next, the proximal end of pigtail 198 is passed through the lumen and elongated member 191, microstimulator 192, and electrode 194 are slid along the length of pigtail 198 until electrode 192 is positioned in or adjacent to a desired anatomical site. Pigtail 198 may include a one-way locking mechanism (e.g., a tine) (not shown) such that the lumen may slide over the locking mechanism as elongated member 191, microstimulator 192, and electrode 194 move distally over the locking mechanism. Once elongated member 191, microstimulator 192, and electrode 194 are disposed distal to the locking mechanism, the locking mechanism activates (e.g., expands) to prevent proximal movement of elongated member 191, microstimulator 192, and electrode 194 past the locking mechanism to keep microstimulator 192 in the desired location and electrode 194 in or adjacent to the desired anatomical site.

Although the medical device described in this disclosure is illustratively an electrode lead, the medical device could readily include an alternative medical device such as a catheter or other generally tubular medical device. Additionally, although the fixation element is described as being configured to be anchored to a muscle or muscle layer, the anchor could be readily configured to be anchored to any convenient anatomical structure which provides a stable location, such as a ligament, joint capsule, fibrous membrane, tendon, fascia, and the like.

It should of course be understood that it is within the scope of this invention to provide bilateral stimulation of the multifidus muscle by electrical stimulation of the tissues that may activate the multifidus such as the medial branch of the dorsal ramus nerve. It further should be understood that multiple levels, for example the medial branch of the dorsal ramus L3, L4 and L5, may be stimulated by leads to train the multifidus muscle to its fullest extent. While the dorsal ramus nerve is described as the targeted nerve for stimulation, it is within the scope of this patent that stimulation of one or more other anatomical structures such as ligaments, tendons, fascia, and/or nerves of other than spine stabilization muscles (e.g., transverse abdominus, psoas, interspinales, longissimus, ileocostalis, intertransversus, quadratus) may comprise adequate therapy.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. An apparatus for neuromuscular electrical stimulation, the apparatus comprising an electrode lead, the electrode lead consisting essentially of:
    an elongated member having a proximal region and a distal region, the distal region having one or more electrodes disposed thereon and an anchoring mechanism, the anchoring mechanism consisting of:
        a first solid polymer flange disposed on the distal region of the elongated member, the first solid polymer flange configured to deploy so as to be angled distally relative to the elongated member, to contact, but not penetrate, tissue to be stimulated without damaging the tissue, and to resist motion of the elongated member in a first direction, wherein the first solid polymer flange is solid during delivery and after deployment; and
        a second solid polymer flange disposed distally relative to the first solid polymer flange on the elongated member, the second solid polymer flange configured to deploy so as to be angled proximally relative to the elongated member and to resist motion of the elongated member in a second direction, wherein the second solid polymer flange is solid during delivery and after deployment,
    wherein at least one of the one or more electrodes is disposed between the first and second solid polymer flanges, and
    wherein the first direction is opposite to the second direction such that the first and second solid polymer flanges sandwich the tissue therebetween to prevent migration proximally, distally, and in rotation, of the elongated member during movement of the tissue to secure the one or more electrodes in or adjacent to tissue innervating one or more spinal muscles within the patient.

2. The apparatus of claim 1, wherein at least one of the one or more electrodes are disposed at the distal region of the elongated member proximal to the first and second solid polymer flanges.

3. The apparatus of claim 1, wherein spacing between the first and second solid polymer flanges is between 2 mm and 10 mm.

4. The apparatus of claim 1, wherein the first and second solid polymer flanges have a length between 1 mm and 5 mm.

5. The apparatus of claim 1, wherein the first solid polymer flange has between 1 and 8 projections.

6. The apparatus of claim 1, wherein the elongated member comprises an elastic section.

7. The apparatus of claim 1, wherein the first and second solid polymer flanges are shaped and sized to sandwich the tissue so as to secure the one or more electrodes in or adjacent to a medial branch of the dorsal rami innervating a multifidus muscle.

8. The apparatus of claim 1, further comprising an implantable pulse generator coupled to the proximal region of the elongated member.

9. The apparatus of claim 1, wherein the first solid polymer flange is shaped and sized to be deployed between muscle layers without damaging the muscle layers.

10. The apparatus of claim 1, wherein the first and second solid polymer flanges have a width between 0.25 mm and 2 mm.

11. The apparatus of claim 1, wherein the first and second solid polymer flanges are a partial flange or a divided flange.

12. The apparatus of claim 1, wherein the tissue comprises a muscle and the first and second solid polymer flanges have a flat surface or a smooth surface, or both, configured to minimize muscle damage.

13. The apparatus of claim 1, wherein the first and second solid polymer flanges are configured to sandwich a muscle layer therebetween.

14. The apparatus of claim 1, wherein the first solid polymer flange or the second solid polymer flange, or both, has three projections.

15. The apparatus of claim 1, further comprising a cap coupled to a distal end of the elongated member of the electrode lead, the cap having a lumen configured to receive a stylet.

16. The apparatus of claim 1, further comprising an implantable micro stimulator coupled to the elongated member of the electrode lead at the proximal region.

17. A method of anchoring an elongated member having one or more electrodes for neuromuscular electrical stimulation, the method comprising:
    providing an elongated member having an anchoring mechanism consisting of first and second solid polymer flanges disposed at a distal region of the elongated member, the first solid polymer flange configured to deploy so as to be angled distally relative to the elongated member, the second solid polymer flange configured to deploy so as to be angled proximally relative to the elongated member and disposed distally relative to the first solid polymer flange;
    inserting the first and second solid polymer flanges against or between muscle layers without damaging the muscle layers so as to sandwich the muscle layers therebetween to secure the one or more electrodes in or adjacent to tissue innervating one or more spinal muscles within a patient and to resist displacement proximally, distally, and in rotation, of the elongated member during movement of the muscle; and maintaining the one or more electrodes in or adjacent to the tissue innervating the one or more spinal muscles using the first and second solid polymer flanges.

18. The method of claim 17, wherein the first and second solid polymer flanges have between 1 and 8 projections.

19. The method of claim 17, further comprising one or more additional electrodes disposed at the distal region of the elongated member proximal to the first and second solid polymer flanges.

20. The method of claim 17, wherein the tissue comprises the medial branch of the dorsal rami, further comprising delivering electrical energy to the dorsal rami with the one or more electrodes.

* * * * *